US008034844B2

(12) United States Patent  
Fox et al.

(10) Patent No.: US 8,034,844 B2
(45) Date of Patent: Oct. 11, 2011

(54) COMPOSITIONS HAVING A HIGH ANTIVIRAL EFFICACY

(75) Inventors: Priscilla S. Fox, Phoenix, AZ (US);
Daniel E. Pedersen, Cottage Grove, MN (US); John J. Rolando, Woodbury, MN (US); Richard K. Staub, Lakeville, MN (US)

(73) Assignee: The Dial Corporation, Scottsdale, AZ (US)

( * ) Notice: Subject to any disclaimer, the term of this patent is extended or adjusted under 35 U.S.C. 154(b) by 527 days.

(21) Appl. No.: 11/807,457

(22) Filed: May 29, 2007

(65) Prior Publication Data

US 2007/0280900 A1 Dec. 6, 2007

Related U.S. Application Data

(60) Provisional application No. 60/809,291, filed on May 30, 2006, provisional application No. 60/811,354, filed on Jun. 6, 2006.

(51) Int. Cl.
*A01N 37/00* (2006.01)
*A61K 31/19* (2006.01)
*A61K 31/765* (2006.01)

(52) U.S. Cl. ............... 514/574; 514/557; 424/78.37

(58) Field of Classification Search ............... 514/574, 514/557; 424/78.37
See application file for complete search history.

(56) References Cited

U.S. PATENT DOCUMENTS

| | | | |
|---|---|---|---|
| 3,393,155 A * | 7/1968 | Schutte et al. | 428/402.2 |
| 3,929,678 A | 12/1975 | Laughlin et al. | |
| 4,503,070 A | 3/1985 | Eby, III | |
| 4,647,458 A | 3/1987 | Ueno et al. | |
| 4,767,788 A | 8/1988 | Diana | |
| 4,970,216 A | 11/1990 | Deckner et al. | |
| 4,975,217 A | 12/1990 | Brown-Skrobot et al. | |
| 5,017,617 A | 5/1991 | Kihara et al. | |
| 5,043,357 A | 8/1991 | Hoffler et al. | |
| 5,049,440 A | 9/1991 | Bornhoeft, III et al. | |
| 5,070,126 A | 12/1991 | Toyonishi et al. | |
| 5,200,189 A | 4/1993 | Oakes et al. | |
| 5,314,687 A | 5/1994 | Oakes et al. | |
| 5,316,688 A | 5/1994 | Gladfelter et al. | |
| 5,389,390 A | 2/1995 | Kross | |
| 5,403,864 A | 4/1995 | Bruch et al. | |
| 5,409,713 A | 4/1995 | Lokkesmoe et al. | |
| 5,409,905 A | 4/1995 | Eby, III | |
| 5,439,681 A | 8/1995 | Khan et al. | |
| 5,525,345 A * | 6/1996 | Warner et al. | 424/402 |
| 5,622,724 A | 4/1997 | Bryce-Smith et al. | |
| 5,629,006 A | 5/1997 | Hoang et al. | |
| 5,635,462 A | 6/1997 | Fendler et al. | |
| 5,639,795 A | 6/1997 | Friedman et al. | |
| 5,714,374 A | 2/1998 | Arnold et al. | |
| 5,718,910 A | 2/1998 | Oakes et al. | |
| 5,728,404 A | 3/1998 | von Rheinbaben et al. | |
| 5,776,430 A | 7/1998 | Osborne et al. | |
| 5,798,329 A | 8/1998 | Taylor et al. | |
| 5,800,827 A | 9/1998 | Igarashi et al. | |
| 5,830,487 A | 11/1998 | Klofta et al. | |
| 5,929,016 A | 7/1999 | Harrison | |
| 5,942,478 A | 8/1999 | Lopes | |
| 5,968,539 A | 10/1999 | Beerse et al. | |
| 6,022,551 A | 2/2000 | Jampani et al. | |
| 6,034,133 A * | 3/2000 | Hendley et al. | 514/573 |
| 6,063,425 A | 5/2000 | Kross et al. | |
| 6,080,417 A | 6/2000 | Kramer et al. | |
| 6,090,772 A | 7/2000 | Kaiser et al. | |
| 6,106,851 A | 8/2000 | Beerse et al. | |
| 6,107,261 A | 8/2000 | Taylor et al. | |
| 6,110,908 A | 8/2000 | Guthery | |
| 6,113,933 A | 9/2000 | Beerse et al. | |
| 6,113,963 A | 9/2000 | Gutzmann et al. | |
| 6,136,771 A | 10/2000 | Taylor et al. | |
| 6,183,807 B1 | 2/2001 | Gutzmann et al. | |
| 6,190,674 B1 | 2/2001 | Beerse et al. | |
| 6,190,675 B1 | 2/2001 | Beerse et al. | |
| 6,204,230 B1 | 3/2001 | Taylor et al. | |
| 6,210,695 B1 | 4/2001 | Beerse et al. | |
| 6,214,363 B1 | 4/2001 | Beerse et al. | |
| 6,217,887 B1 | 4/2001 | Beerse et al. | |
| 6,248,343 B1 | 6/2001 | Jampani et al. | |
| 6,294,186 B1 | 9/2001 | Beerse et al. | |
| 6,358,906 B1 | 3/2002 | Ochs et al. | |
| 6,376,437 B2 | 4/2002 | Viscovitz et al. | |
| 6,432,906 B1 | 8/2002 | Carlson et al. | |
| 6,436,885 B2 | 8/2002 | Biedermann et al. | |
| 6,451,748 B1 | 9/2002 | Taylor et al. | |
| 6,475,501 B1 | 11/2002 | Kelly et al. | |
| 6,488,942 B1 | 12/2002 | Ingemann et al. | |
| 6,514,556 B2 | 2/2003 | Hilgren et al. | |
| 6,517,849 B1 | 2/2003 | Seger et al. | |
| 6,545,047 B2 | 4/2003 | Gutzmann et al. | |
| 6,551,553 B1 | 4/2003 | von Rheinbaben et al. | |
| 6,559,110 B1 | 5/2003 | Lopes | |
| 6,608,121 B2 | 8/2003 | Isozaki et al. | |
| 6,610,314 B2 | 8/2003 | Koenig et al. | |
| 6,632,291 B2 | 10/2003 | Rabon et al. | |
| 6,657,004 B2 | 12/2003 | Mizutani | |
| 6,673,835 B1 | 1/2004 | Hensley et al. | |
| 6,787,512 B1 | 9/2004 | Verrall et al. | |

(Continued)

FOREIGN PATENT DOCUMENTS

EP 0208403 B1 1/1990

(Continued)

OTHER PUBLICATIONS

Allawala et al., "The release of antimicrobial agents from solutions of surface-active agents," *J. Am. Pharm. Assoc.*, 42:267-275 (1953).

(Continued)

*Primary Examiner* — Shengjun Wang
*Assistant Examiner* — Samira Jean-Louis
(74) *Attorney, Agent, or Firm* — Marshall, Gerstein & Borun LLP (57) ABSTRACT

Antiviral compositions having a rapid antiviral effectiveness, and a persistent antiviral effectiveness, are disclosed. The antimicrobial compositions contain (a) a powdered solid substrate and (b) an organic acid.

39 Claims, 1 Drawing Sheet

U.S. PATENT DOCUMENTS

| | | | |
|---|---|---|---|
| 6,855,341 | B2 | 2/2005 | Smith |
| 6,858,232 | B2 | 2/2005 | Verbiscar |
| 6,921,529 | B2 | 7/2005 | Maley |
| 6,956,070 | B2 | 10/2005 | Fujiwara et al. |
| 7,005,451 | B1 | 2/2006 | Nevermann et al. |
| 7,026,308 | B1* | 4/2006 | Gavin et al. .................. 514/188 |
| 7,208,453 | B2 | 4/2007 | Nevermann et al. |
| 7,268,163 | B2 | 9/2007 | Konowalchuk et al. |
| 7,592,300 | B2 | 9/2009 | Taylor et al. |
| 2001/0053378 | A1 | 12/2001 | Chilakos |
| 2002/0098159 | A1 | 7/2002 | Wei et al. |
| 2002/0161046 | A1 | 10/2002 | Konowalchuk et al. |
| 2002/0165277 | A1 | 11/2002 | Konowalchuk et al. |
| 2002/0165279 | A1 | 11/2002 | Konowalchuk et al. |
| 2002/0182348 | A1 | 12/2002 | Fujiwara et al. |
| 2003/0175323 | A1 | 9/2003 | Utterberg et al. |
| 2003/0235550 | A1 | 12/2003 | Pan et al. |
| 2004/0001797 | A1 | 1/2004 | Saud et al. |
| 2004/0086575 | A1 | 5/2004 | Smith |
| 2004/0096521 | A1 | 5/2004 | Clawson |
| 2004/0214785 | A1 | 10/2004 | Dees et al. |
| 2004/0234457 | A1 | 11/2004 | Rennie et al. |
| 2005/0013836 | A1 | 1/2005 | Raad |
| 2005/0042240 | A1 | 2/2005 | Utterberg et al. |
| 2005/0159321 | A1 | 7/2005 | Cusack et al. |
| 2005/0203187 | A1 | 9/2005 | Verbiscar |
| 2005/0232868 | A1 | 10/2005 | Rennie et al. |
| 2005/0232895 | A1 | 10/2005 | Chen |
| 2005/0238728 | A1 | 10/2005 | Evans |
| 2005/0271711 | A1 | 12/2005 | Lynch et al. |
| 2007/0274940 | A1* | 11/2007 | Fuls et al. .................. 424/70.1 |

FOREIGN PATENT DOCUMENTS

| | | |
|---|---|---|
| EP | 0375827 | 7/1990 |
| EP | 0394928 A1 | 10/1990 |
| EP | 0444230 | 9/1991 |
| EP | 0505935 | 9/1992 |
| EP | 0604848 | 7/1994 |
| EP | 0651048 | 5/1995 |
| EP | 0707794 | 4/1996 |
| EP | 0251303 | 1/1998 |
| EP | 0937394 | 8/1999 |
| EP | 1158016 | 11/2001 |
| EP | 1180536 | 2/2002 |
| EP | 1251147 | 10/2002 |
| FR | 1568905 A | 5/1969 |
| GB | 933684 A | 8/1963 |
| GB | 1126953 | 9/1968 |
| GB | 2187097 A | 9/1987 |
| GB | 2231496 A | 11/1990 |
| GB | 2391810 | 2/2004 |
| JP | 07252105 A | 10/1995 |
| JP | 10087410 A | 4/1998 |
| SE | 466111 | 12/1991 |
| WO | WO-91/19222 | 12/1991 |
| WO | WO-93/07250 | 4/1993 |
| WO | WO-93/16597 | 9/1993 |
| WO | WO-95/09605 | 4/1995 |
| WO | WO-95/32705 | 12/1995 |
| WO | WO-96/06152 | 2/1996 |
| WO | WO96/11572 A1 | 4/1996 |
| WO | WO-96/24247 | 8/1996 |
| WO | WO-96/29867 | 10/1996 |
| WO | WO-97/15647 | 5/1997 |
| WO | WO-97/46218 | 12/1997 |
| WO | WO-98/01110 | 1/1998 |
| WO | WO-98/44792 | 10/1998 |
| WO | WO-98/44794 | 10/1998 |
| WO | WO-98/55096 | 12/1998 |
| WO | WO-99/20228 | 4/1999 |
| WO | WO00/27192 A1 | 5/2000 |
| WO | WO-00/43047 | 7/2000 |
| WO | WO-00/78141 | 12/2000 |
| WO | WO-00/78275 | 12/2000 |
| WO | WO-01/28337 | 4/2001 |
| WO | WO-01/28338 | 4/2001 |
| WO | WO-01/28339 | 4/2001 |
| WO | WO-01/28340 | 4/2001 |
| WO | WO01/41567 A1 | 6/2001 |
| WO | WO01/41573 A1 | 6/2001 |
| WO | WO-01/79417 | 10/2001 |
| WO | WO02/059244 A2 | 8/2002 |
| WO | WO02/069887 A2 | 9/2002 |
| WO | WO02/078667 A1 | 10/2002 |
| WO | WO-04/000016 | 12/2003 |
| WO | WO-2004/004677 | 1/2004 |
| WO | WO-2004/016087 | 2/2004 |
| WO | WO-2004/021786 | 3/2004 |
| WO | WO-2004/080179 | 9/2004 |
| WO | WO-2004/086575 | 10/2004 |
| WO | WO-2005/074947 | 8/2005 |
| WO | WO2006/062857 A2 | 6/2006 |
| WO | WO-2007/095008 | 8/2007 |
| ZA | 200308879 | 5/2004 |

OTHER PUBLICATIONS

Hayden et al., "Inactivation of rhinovirus on human fingers by virucidal activity of glutaric acid," *Antimicrob. Agents Chemother.*, 26:928-929 (1984).

Hayden et al., "The effect of placebo and virucidal paper handkerchiefs on viral contamination of the hand and transmission of experimental rhinoviral infection," *J. Infect. Dis.*, 152:403-407 (1985).

International Search Report for international application No. PCT/US2005/043720, dated Oct. 6, 2006.

International Search Report for international application No. PCT/US2005/043765, dated Sep. 28, 2006.

International Search Report for international application No. PCT/US2005/043766, dated Oct. 12, 2006.

International Search Report for international application No. PCT/US2005/043767, dated Oct. 4, 2006.

International Search Report for international application No. PCT/US2005/043794, dated Sep. 28, 2006.

International Search Report for international application No. PCT/US2005/043910, dated Apr. 2, 2007.

International Search Report for international application No. PCT/US2005/043921, dated Oct. 17, 2006.

Mitchell, "Bactericidal activity of chloroxylenol in aqueous solutions of cetomacrogol," J. Pharm. Pharmacol., 16:533-537 (1964).

Sattar et al., "Chemical disinfection to interrupt transfer of rhinovirus type 14 from environmental surfaces to hands," *Appl. Environ. Microbiol.*, 59:1579-1585 (1993).

Written Opinion of the International Searching Authority for international application No. PCT/US2005/043921, dated Oct. 17, 2006.

Written Opinion of the International Searching Authority for international application No. PCT/US2005/043720, dated Jun. 21, 2007.

Written Opinion of the International Searching Authority for international application No. PCT/US2005/043765, dated Sep. 28, 2006.

Written Opinion of the International Searching Authority for international application No. PCT/US2005/043766, dated Oct. 12, 2006.

Written Opinion of the International Searching Authority for international application No. PCT/US2005/043767, dated Oct. 4, 2006.

Written Opinion of the International Searching Authority for international application No. PCT/US2005/043794, dated Sep. 28, 2006.

Written Opinion of the International Searching Authority for international application No. PCT/US2005/043910, dated Apr. 12, 2007.

International Search Report in PCT/US2007/012647, filed Aug. 4, 2008.

Poli, et al., "Virucidal Activity of Organic Acids," *FD. Chem.* pp. 251-258 (1979).

Haley et al, Bactericidal Activity of Antiseptics Against Methicillin-Resistant *Staphylococcus aureus*, Journal of Clinical Microbiology, vol. 21, No. 6, 1985, p. 991-992.

Kramer et al, Virucidal Activity of a New Hand Disinfectant With Reduced Ethanol Content: Comparison With Other Alcohol-Based Formulations, J.of Hospital Infection, 62, 98-106.

McKeough et al, Comparison of New Topical Treatments for Herpes Labialis, Arch Dermatol, 2001, vol. 137, p. 1153-1158.

Malik et al, Comparative Efficacy of Ethanol and Isopropanol Against Feline Calicivirus, a Norovirus Surrogate, Amer. Jour. of Infec. Cont., 34(1):31-35 (2006).

International Search Report for international application No. PCT/US2007/012318, dated Jul. 2, 2008.
International Search Report for international application No. PCT/US2007/012321, dated Jul. 3, 2008.
International Search Report for international application No. PCT/US2007/012331, dated Jul. 2, 2008.
International Search Report for international application No. PCT/US2007/012735, dated Jul. 2, 2008.
International Search Report for international application No. PCT/US2007/012794, dated Jul. 1, 2008.
International Search Report for international application No. PCT/US2007/013136, dated Jul. 2, 2008.
Database WPI Week 199202 Derwent Publications Ltd., London, GB; AN 1989-1 36366 XP002429055 & SE 466111B (ASTRA AB) Dec. 16, 1991.

* cited by examiner

COMPOSITIONS HAVING A HIGH ANTIVIRAL EFFICACY

CROSS-REFERENCE TO RELATED APPLICATIONS

This application claims the benefit of U.S. Provisional Patent Application 60/809,291, filed May 30, 2006, and U.S. Provisional Patent Application 60/811,354, filed Jun. 6, 2006.

FIELD OF THE INVENTION

The present invention relates to antiviral compositions having a rapid and persistent antiviral effectiveness. More particularly, the present invention relates to antiviral compositions comprising (a) a powdered solid substrate and (b) an organic acid. The combination of (a) and (b) provides a solid composition that, when applied directly to a surface, can inactivate or destroy viruses, such as rhinoviruses and rotaviruses. The compositions provide a substantial reduction in nonenveloped viral populations, and influenza viruses, within one minute. In some embodiments, the compositions provide a barrier layer, or film, comprising the organic acid on a treated surface to impart a persistent antiviral activity to the surface.

BACKGROUND OF THE INVENTION

Human health is impacted by a variety of microbes encountered on a daily basis. In particular, contact with various microbes in the environment can lead to an illness, possibly severe, in mammals. For example, microbial contamination can lead to a variety of illnesses, including, but not limited to, food poisoning, a streptococcal infection, anthrax (cutaneous), athlete's foot, cold sores, conjunctivitis ("pink eye"), coxsackievirus (hand-foot-mouth disease), croup, diphtheria (cutaneous), ebolic hemorrhagic fever, and impetigo.

It is known that washing body parts (e.g., hand washing) and inanimate surfaces (e.g., countertops and sinks) can significantly decrease the population of microorganisms, including pathogens. Therefore, cleaning skin and other animate and inanimate surfaces to reduce microbial populations is a first defense in removing such pathogens from these surfaces, and thereby minimizing the risk of infection.

Viruses are a category of pathogens of primary concern. Viral infections are among the greatest causes of human morbidity, with an estimated 60% or more of all episodes of human illness in developed countries resulting from a viral infection. In addition, viruses infect virtually every organism in nature, with high virus infection rates occurring among all mammals, including humans, pets, livestock, and zoo specimens.

Viruses exhibit an extensive diversity in structure and life cycle. A detailed description of virus families, their structures, life cycles, and modes of viral infection is discussed in *Fundamental Virology*, 4th Ed., Eds. Knipe & Howley, Lippincott Williams & Wilkins, Philadelphia, Pa., 2001.

Simply stated, virus particles are intrinsic obligate parasites, and have evolved to transfer genetic material between cells and encode sufficient information to ensure their propagation. In a most basic form, a virus consists of a small segment of nucleic acid encased in a simple protein shell. The broadest distinction between viruses is the enveloped and nonenveloped viruses, i.e., those that do or do not contain, respectively, a lipid-bilayer membrane.

Viruses propagate only within living cells. The principal obstacle encountered by a virus is gaining entry into the cell, which is protected by a cell membrane of thickness comparable to the size of the virus. In order to penetrate a cell, a virus first must become attached to the cell surface. Much of the specificity of a virus for a certain type of cell lies in its ability to attach to the surface of that specific cell. Durable contact is important for the virus to infect the host cell, and the ability of the virus and the cell surface to interact is a property of both the virus and the host cell. The fusion of viral and host-cell membranes allows the intact viral particle, or, in certain cases, only its infectious nucleic acid to enter the cell. Therefore, in order to control a viral infection, it is important to rapidly kill a virus that contacts the skin, and ideally to provide a persistent antiviral activity on the skin, or inanimate surface, in order to control viral infections.

For example, rhinoviruses, influenza viruses, and adenoviruses are known to cause respiratory infections. Rhinoviruses are known to cause respiratory infections. Rhinoviruses are members of the picornavirus family, which is a family of "naked viruses" that lack an outer envelope. The human rhinoviruses are so termed because of their special adaptation to the nasopharyngeal region, and are the most important etiological agents of the common cold in adults and children. Officially there are 102 rhinoviruses serotypes. Most of the picornaviruses isolated from the human respiratory system are acid labile, and this lability has become a defining characteristic of rhinoviruses.

Rhinovirus infections are spread from person to person by direct contact with virus-contaminated respiratory secretions. Typically, this contact is in the form of physical contact with a contaminated surface, rather than via inhalation of airborne viral particles.

Rhinovirus can survive on environmental surfaces for hours after initial contamination, and infection is readily transmitted by finger-to-finger contact, and by contaminated environmental surface-to-finger contact, if the newly contaminated finger then is used to rub an eye or touch the nasal mucosa. Therefore, virus contamination of skin and environmental surfaces should be minimized to reduce the risk of transmitting the infection to the general population.

Several gastrointestinal infections also are caused by viruses, particularly rotaviruses and noroviruses. For example, Norwalk virus causes nausea, vomiting (sometimes accompanied by diarrhea), and stomach cramps. This infection typically is spread from person to person by direct contact. Acute hepatitis A viral infection similarly can be spread by direct contact between one infected person and a nonimmune individual by hand-to-hand, hand-to-mouth, or aerosol droplet transfer, or by indirect contact when an uninfected individual comes into contact with a hepatitis A virus-contaminated solid object. Numerous other viral infections are spread similarly. The risk of transmitting such viral infections can be reduced significantly by inactivating or removing viruses from the hands and other environmental surfaces.

Common household phenol/alcohol disinfectants are effective in disinfecting contaminated environmental surfaces, but lack persistent virucidal activity. Hand washing is highly effective in disinfecting contaminated fingers, but again suffers from a lack of persistent activity. These shortcomings illustrate the need for improved virucidal compositions having a persistent activity against viruses, such as rhinoviruses and rotaviruses.

Antimicrobial personal care compositions are known in the art. In particular, antibacterial cleansing compositions, which typically are used to cleanse the skin and to destroy bacteria present on the skin, especially the hands, arms, and face of the user, are well-known commercial products.

Antibacterial compositions are used, for example, in the health care industry, food service industry, meat processing industry, and in the private sector by individual consumers. The widespread use of antibacterial compositions indicates the importance consumers place on controlling bacteria populations on skin. The paradigm for antibacterial compositions is to provide a substantial and broad spectrum reduction in bacterial populations quickly and without adverse side effects associated with toxicity and skin irritation. Such antibacterial compositions are disclosed in U.S. Pat. Nos. 6,107,261 and 6,136,771, each incorporated herein by reference.

One class of antibacterial personal care compositions is the hand sanitizer. This class of compositions is used primarily by medical personnel to disinfect the hands and fingers. A hand sanitizer is applied to, and rubbed into, the hands and fingers, and the composition is allowed to evaporate from the skin.

Hand sanitizers contain a high percentage of an alcohol, like ethanol. At the high percent of alcohol present in the composition, the alcohol itself acts as a disinfectant. In addition, the alcohol quickly evaporates to obviate wiping or rinsing skin treated with the hand sanitizer. Hand sanitizers containing a high percentage of an alcohol, i.e., about 40% or greater by weight of the composition, do not provide a persistent bacterial kill.

Antibacterial cleansing compositions typically contain an active antibacterial agent, a surfactant, and various other ingredients, for example, dyes, fragrances, pH adjusters, thickeners, skin conditioners, and the like, in an aqueous and/or alcoholic carrier. Several different classes of antibacterial agents have been used in antibacterial cleansing compositions. Examples of antibacterial agents include a bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and triclosan (i.e., 2,4,4'-trichloro-2'-hydroxy-diphenylether). Antimicrobial compositions based on such antibacterial agents exhibit a wide range of antibacterial activity, ranging from low to high, depending on the microorganism to be controlled and the particular antibacterial composition. Most commercial antibacterial compositions generally offer a low to moderate antibacterial activity, and no reported antiviral activity.

Antimicrobial activity is assessed as the log reduction, or alternatively the percent reduction, in microbial populations provided by the antimicrobial composition. A 1-3 log reduction is preferred, a log reduction of 3-5 is most preferred, whereas a log reduction of less than 1 is least preferred, for a particular contact time, generally ranging from 15 seconds to 5 minutes. Thus, a highly preferred antimicrobial composition exhibits a 3-5 log reduction against a broad spectrum of microorganisms in a short contact time.

Virus control poses a more difficult problem than bacterial control. By sufficiently reducing bacterial populations, the risk of bacterial infection is reduced to acceptable levels. Therefore, a rapid antibacterial kill is desired. With respect to viruses, however, not only is a rapid kill desired, but a persistent antiviral activity also is required. This difference is because merely reducing a virus population is insufficient to reduce infection. In theory, a single virus can cause infection. Therefore, an essentially total, and persistent, antiviral activity is required, or at least desired, for an effective antiviral cleansing composition.

U.S. Pat. No. 6,110,908 discloses a topical antiseptic containing a $C_{2-3}$ alcohol, a free fatty acid, and zinc pyrithione.

U.S. Pat. No. 5,776,430 discloses a topical antimicrobial cleaner containing chlorhexidine and an alcohol. The compositions contain about 50% to 60%, by weight, denatured alcohol and about 0.65% to 0.85%, by weight, chlorhexidine. The composition is applied to the skin, scrubbed into the skin, then rinsed from the skin.

WO 98/01110 discloses compositions comprising triclosan, surfactants, solvents, chelating agents, thickeners, buffering agents, and water. WO 98/01110 is directed to reducing skin irritation by employing a reduced amount of surfactant.

U.S. Pat. No. 5,635,462 discloses compositions comprising PCMX and selected surfactants. The compositions disclosed therein are devoid of anionic surfactants and nonionic surfactants.

EP 0 505 935 discloses compositions containing PCMX in combination with nonionic and anionic surfactants, particularly nonionic block copolymer surfactants.

WO 95/32705 discloses a mild surfactant combination that can be combined with antibacterial compounds, like triclosan.

WO 95/09605 discloses antibacterial compositions containing anionic surfactants and alkylpolyglycoside surfactants.

WO 98/55096 discloses antimicrobial wipes having a porous sheet impregnated with an antibacterial composition containing an active antimicrobial agent, an anionic surfactant, an acid, and water, wherein the composition has a pH of about 3.0 to about 6.0.

N. A. Allawala et al., J. Amer. Pharm. Assoc.—Sci. Ed., Vol. XLII, no. 5, pp. 267-275 (1953) discusses the antibacterial activity of active antibacterial agents in combination with surfactants.

A. G. Mitchell, J. Pharm. Pharmacol., Vol. 16, pp. 533-537 (1964) discloses compositions containing PCMX and a nonionic surfactant that exhibit antibacterial activity.

With respect to hand sanitizer gels, U.S. Pat. No. 5,776,430 discloses a topical antimicrobial cleaner containing chlorhexidine and an alcohol. The compositions contain about 50% to 60%, by weight, denatured alcohol and about 0.65% to 0.85%, by weight, chlorhexidine. The composition is applied to the skin, scrubbed into the skin, then rinsed from the skin.

European Patent Application 0 604 848 discloses a gel-type hand disinfectant containing an antimicrobial agent, 40% to 90% by weight of an alcohol, and a polymer and a thickening agent in a combined weight of not more than 3% by weight. The gel is rubbed into the hands and allowed to evaporate to provide disinfected hands. As illustrated in EP 0 604 848, the amount and identity of the antibacterial agent is not considered important because the hand sanitizer gels contain a high percentage of an alcohol to provide antibacterial activity.

In general, hand sanitizer gels typically contain: (a) at least 60% by weight ethanol or a combination of lower alcohols, such as ethanol and isopropanol, (b) water, (c) a gelling polymer, such as a crosslinked polyacrylate material, and (d) other ingredients, such as skin conditioners, fragrances, and the like. Hand sanitizer gels are used by consumers to effectively sanitize the hands, without, or after, washing with soap and water, by rubbing the hand sanitizer gel on the surface of the hands. Current commercial hand sanitizer gels rely on high levels of alcohol for disinfection and evaporation, and thus suffer from disadvantages. Specifically, because of the volatility of ethanol, the primary antimicrobial agent does not remain on the skin after use, thus failing to provide a persistent antimicrobial effect.

At alcohol concentrations below 60%, ethanol is not recognized as an antiseptic. Thus, in compositions containing less than 60% alcohol, an additional antimicrobial compound is present to provide antimicrobial activity. Prior disclosures, however, have not addressed the issue of which composition ingredient in such an antimicrobial composition provides microbe control. Therefore, for formulations containing a reduced alcohol concentration, the selection of an antimicrobial agent that provides both a rapid antimicrobial effect and a persistent antimicrobial benefit is difficult.

U.S. Pat. Nos. 6,107,261 and 6,136,771 disclose highly effective antibacterial compositions containing a phenolic antimicrobial agent. These patents disclose compositions that solve the problem of controlling bacteria on skin and hard surfaces, but are silent with respect to controlling viruses.

U.S. Pat. Nos. 5,968,539; 6,106,851; and 6,113,933 disclose antibacterial compositions having a pH of about 3 to about 6. The compositions contain an antibacterial agent, an anionic surfactant, and a proton donor.

Antiviral compositions disclosed as inactivating or destroying pathogenic viruses, including rhinovirus, rotavirus, influenza virus, parainfluenza virus, respiratory syncytial virus, and Norwalk virus, also are known. For example, U.S. Pat. No. 4,767,788 discloses the use of glutaric acid to inactivate or destroy viruses, including rhinovirus. U.S. Pat. No. 4,975,217 discloses compositions containing an organic acid and an anionic surfactant, for formulation as a soap or lotion, to control viruses. U.S. Patent Publication 2002/0098159 discloses the use of a proton donating agent and a surfactant, including an antibacterial surfactant, to effect antiviral and antibacterial properties.

U.S. Pat. No. 6,034,133 discloses a virucidal hand lotion containing malic acid, citric acid, and a $C_{1-6}$ alcohol. U.S. Pat. No. 6,294,186 discloses combinations of a benzoic acid analog, such as salicyclic acid, and selected metal salts as being effective against viruses, including rhinovirus. U.S. Pat. No. 6,436,885 discloses a combination of known antibacterial agents with 2-pyrrolidone-5-carboxylic acid, at a pH of 2 to 5.5, to provide antibacterial and antiviral properties. U.S. Pat. No. 6,110,908 discloses a topical antiseptic containing a $C_{2-3}$ alcohol, a free fatty acid, and zinc pyrithione.

Organic acids in personal washing compositions also have been disclosed. For example, WO 97/46218 and WO 96/06152 disclose the use of organic acids or salts, hydrotropes, triclosan, and hydric solvents in a surfactant base for antimicrobial cleansing compositions. These publications are silent with respect to antiviral properties.

Hayden et al., *Antimicrobial Agents and Chemotherapy*, 26:928-929 (1984), discloses interrupting the hand-to-hand transmission of rhinovirus colds through the use of a hand lotion having residual virucidal activity. The hand lotions, containing 2% glutaric acid, were more effective than a placebo in inactivating certain types of rhinovirus. However, the publication discloses that the glutaric acid-containing lotions were not effective against a wide spectrum of rhinovirus serotypes.

A virucidal tissue designed for use by persons infected with the common cold, and including citric acid, malic acid, and sodium lauryl sulfate, is known. Hayden et al., *Journal of Infectious Diseases*, 152:493-497 (1985), however, reported that use of paper tissues, either treated with virus-killing substances or untreated, can interrupt the hand-to-hand transmission of viruses. Hence, no distinct advantage in preventing the spread of rhinovirus colds can be attributed to the compositions incorporated into the virucidal tissues.

An efficacious antimicrobial composition effective against both bacteria and viruses has been difficult to achieve because of the fundamental differences between a bacteria and a virus. Although a number of antimicrobial cleansing products currently exist, taking a variety of product forms (e.g., deodorant soaps, hard surface cleaners, and surgical disinfectants), such antimicrobial products typically incorporate antimicrobial agents, e.g., a phenolic compound, and/or harsh surfactants, which can dry out and irritate skin tissues. The above-discussed antimicrobial and antiviral compositions are liquid or gel compositions that when applied frequently can irritate the skin. Ideally, personal cleansing products gently cleanse the skin, cause little or no irritation, and do not leave the skin overly dry after frequent use.

Accordingly, a need exists for an antimicrobial composition that is highly efficacious against a broad spectrum of viruses in a short time period, and wherein the composition can provide a persistent and broad spectrum antiviral activity, and is mild to the skin. Personal care products demonstrating improved mildness and a heightened level of viral reduction are provided by the powdered antimicrobial compositions of the present invention.

SUMMARY OF THE INVENTION

The present invention is directed to antimicrobial compositions that provide a rapid and a persistent antiviral effectiveness in less than about one minute. More particularly, the present invention relates to solid antimicrobial compositions containing (a) a powdered, solid substrate, such as a hydrated substrate, like "dry water" and (b) an organic acid. The solid antimicrobial compositions can contain an optional active antibacterial agent, such as a phenolic and/or a quaternary ammonium antibacterial agent, for example. A present solid composition is free of intentionally added cleansing surfactants, such as anionic, cationic, and ampholytic surfactants. In preferred embodiments, the composition is capable of providing a residual layer of the organic acid on a treated surface.

As discussed hereafter, a present solid antimicrobial composition provides a rapid and persistent control of nonenveloped viruses regardless of the log P of the organic acid. In one embodiment, the organic acid has a water-octanol partition coefficient, expressed as log P, of less than one, and the composition exhibits a high activity against nonenveloped viruses. In another embodiment, the organic acid has a log P of one or greater, and the composition exhibits an antiviral activity and an antibacterial activity.

Accordingly, one aspect of the present invention is to provide a solid antimicrobial composition that is highly effective at inactivating or destroying viruses harmful to human health, particularly nonenveloped viruses, like acid-labile viruses, and especially rhinoviruses. The present solid compositions also are efficacious against influenza viruses and noroviruses.

Another aspect of the present invention is to provide a solid antimicrobial composition comprising:

(a) a powdered solid substrate, like a silica material capable of containing several times its weight in water (e.g., dry water), or a clay; and (b) a virucidally effective amount of one or more organic acid. The solid antimicrobial composition also can contain optional ingredients, like an active antibacterial agent and ingredients that enhance the esthetics and efficacy of the composition, e.g., emollients, alcohols, polyhydric alcohols, and fragrances.

In preferred embodiments, the composition provides an essentially continuous layer or film of the organic acid on a treated surface to impart a persistent antiviral activity to the treated surface.

Yet another aspect of the present invention is to provide a solid antiviral composition that exhibits a substantial, broad spectrum, and persistent virus control. The solid composition can be in the form of solid particles, e.g., a powder; a compressed sheet; or other solid or semisolid form capable of retaining its shape when left to stand unsupported for at least one hour, e.g., a paste. The solid antiviral composition can be used as is, or can be used as a component in a liquid, gel, semisolid, or solid composition.

Another aspect of the present invention is to provide a solid antiviral composition comprising (a) a powdered solid substrate and (b) an organic acid that is substantive to the skin, and/or that fails to penetrate the skin, and/or that resists rinsing from the skin, and/or that forms an essentially continuous barrier layer on the skin. Such organic acids typically have a log P of less than one, and the compositions exhibit a substantial activity against viruses. The persistent antiviral activity is attributed, in part, to a residual layer or film of the organic acid on treated skin, which resists removal from the skin after several rinsings, and during normal daily routines for a period of several hours.

The organic acid can be, for example, hydrophobic monocarboxylic acids, polycarboxylic acids, polymeric acids having a plurality of carboxylic, phosphate, sulfonate, and/or sulfate moieties, or mixtures thereof. The organic acids preferably have a log P of less than one, and the solid compositions are effective against a broad spectrum of nonenveloped viruses, influenza viruses, and rotaviruses. The solid compositions do not dry or irritate the skin, thus overcoming a major problem found in liquid and gelled hand sanitizers.

Still another aspect of the present invention is to provide a solid antiviral composition having antiviral activity comprising (a) a powdered solid substrate and (b) an organic acid selected from the group consisting of monocarboxylic acids, polycarboxylic acids, polymeric acids having a plurality of carboxylic, phosphate, sulfonate, and/or sulfate moieties, or mixtures thereof, wherein the organic acid has a log P of one or greater. These solid compositions provide an effective and persistent control of nonenveloped viruses and influenza viruses.

Preferred compositions comprise one or more polycarboxylic acid, and more preferably also include a polymeric acid. These compositions provide an effective and persistent control of viruses.

Another aspect of the present invention is to provide an antimicrobial composition that resists rinsing from the skin, e.g., at least 50%, at least 60%, and preferably at least 70% of the nonvolatile components of an applied composition remains on a treated surface after three water rinsings and an effective antiviral amount of the composition remains on the skin after ten water rinsings.

Another aspect of the present invention is to provide an antiviral composition that exhibits a log reduction against nonenveloped viruses, such as acid-labile viruses, including rhinovirus serotypes, such as Rhinovirus 1a, Rhinovirus 2, Rhinovirus 14, and Rhinovirus 4, and against rotavirus serotypes, such as Rotavirus Wa, of at least 4 after 30 seconds of contact. The antimicrobial composition also provides a log reduction against nonenveloped viruses of about 3 for at least about five hours, and at least 2 for about six hours, after application with a 30 second contact time. In some embodiments, the antimicrobial composition provides a log reduction of 2 against nonenveloped viruses for up to about eight hours.

Another aspect of the present invention is to provide consumer products based on a solid antiviral composition of the present invention, for example, a wound care agent, a hand sanitizer, a disinfectant, and the like. A solid composition of the present invention is a leave-on product. The composition is allowed to remain on the skin to provide a persistent antiviral activity. The present compositions are esthetically pleasing and nonirritating to the skin. Embodiments containing a hydrated solid substrate liquefy upon application and rubbing onto the skin, which helps provide a continuous layer of the composition on the skin. The solid composition also can be applied to, or sniffed into, the nasal cavities to destroy and inactivate viruses.

Yet another aspect of the present invention is to provide a composition and method of interrupting transmission of a virus from animate surfaces, like human fingers, to human nasal mucosa. Especially provided is a method and composition for controlling the transmission of nonenveloped viruses, particularly rhinovirus, either by preventing viruses from entering nasal cavities or by effectively controlling viruses introduced into nasal cavities, for example, by contact with a contaminated hand or finger, and continuing to control the viruses for a period of about four or more hours, and up to about 12 hours, after application of the composition to the skin on or surrounding the nose, including a nasal cavity.

The present invention also is capable of interrupting the transmission of virus from an inanimate to an animate surface by contacting an inanimate surface with a solid composition of the present invention. The composition can be applied directly to an inanimate surface, or via an applicator, such as a web material.

Another aspect of the present invention is to provide a dispensing device, preferably hand held, comprising a reservoir of a present solid antimicrobial composition, wherein the device is adapted to dispense the composition onto animate surfaces, such as onto the nose and surrounding facial area, and/or into a human nostril or onto inanimate surfaces.

A further aspect of the present invention is to provide a method of quickly controlling a wide spectrum of viruses on animal tissue, including human tissue, by contacting the tissue, like the dermis, with a solid composition of the present invention to reduce viral population levels to a desired level. A further aspect of the present invention is to provide a composition that imparts a persistent control of viruses on animal tissue.

Still another aspect of the present invention is to provide a method of treating or preventing virus-mediated diseases and conditions caused by rhinoviruses, rotaviruses, picomaviruses, adenoviruses, herpes viruses, respiratory syncytial viruses (RSV), coronaviruses, enteroviruses, and other nonenveloped viruses. The present method and composition also prevent diseases and conditions mediated by influenza viruses.

Yet another aspect of the present invention is to provide a composition and method of interrupting transmission of a virus from animate and inanimate surfaces to an animate surface, especially human skin. Especially provided is a method and composition for controlling the transmission of nonenveloped viruses, particularly rhinovirus, by effectively controlling viruses present on human skin and continuing to control the viruses for a period of about four or more hours, and up to about eight hours, after application of the composition to the skin.

These and other novel aspects and advantages of the present invention are set forth in the following, nonlimiting detailed description of the preferred embodiments.

DETAILED DESCRIPTION OF THE PREFERRED EMBODIMENTS

Personal care products incorporating an active antimicrobial agent have been known for many years. Since the introduction of antimicrobial personal care products, many claims have been made that such products provide antimicrobial properties. To be most effective, an antimicrobial composition should provide a high log reduction against a broad spectrum of organisms in as short a contact time as possible. Ideally, the composition also should inactivate viruses.

As presently formulated, most commercial liquid antibacterial soap compositions provide a poor to marginal time kill efficacy, i.e., rate of killing bacteria. These compositions do not effectively control viruses.

Antimicrobial hand sanitizer compositions typically do not contain a surfactant and rely upon a high concentration of an alcohol to control bacteria. The alcohols evaporate and, therefore, cannot provide a persistent bacterial control. The alcohols also can dry and irritate the skin.

Most current products especially lack efficacy against Gram negative bacteria, such as E. coli, which are of particular concern to human health. Compositions do exist, however, that have an exceptionally high broad spectrum antibacterial efficacy, as measured by a rapid kill of bacteria (i.e., time kill), which is to be distinguished from persistent kill. These products also lack a sufficient antiviral activity.

The present antimicrobial compositions are solid compositions, provide an excellent broad spectrum antiviral efficacy, and significantly improve antiviral efficacy compared to prior liquid compositions that incorporate a high percentage of an alcohol, i.e., 40% or greater, by weight. The basis of this improved efficacy is (a) the discovery that an organic acid, and especially an organic acid having a log P of less than about 1, substantially improves antiviral efficacy, and (b) the pH of an animate surface after application of the composition to the surface. An important aspect of the present invention is to maintain a low skin pH for an extended time to provide a persistent antiviral activity. In preferred embodiments, this is achieved by forming an essentially continuous film of the nonvolatile composition components on the skin, which provides a reservoir of the organic acids to maintain a low skin pH. The solid compositions also are mild to the skin and overcome the skin irritation problems of prior liquid antimicrobial compositions.

Figure 1A:
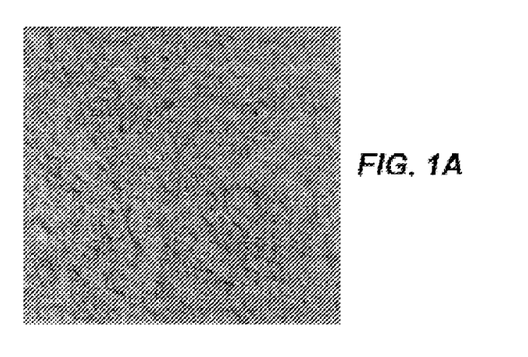
FIGS. 1*a* and 1*b* are reflectance micrographs showing a barrier layer of nonvolatile components on a surface provided by application of a composition of the present invention to the surface.
Figure 1B:
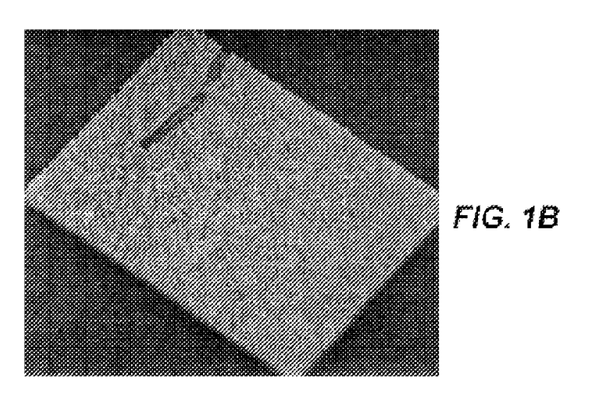
Figure 1C:
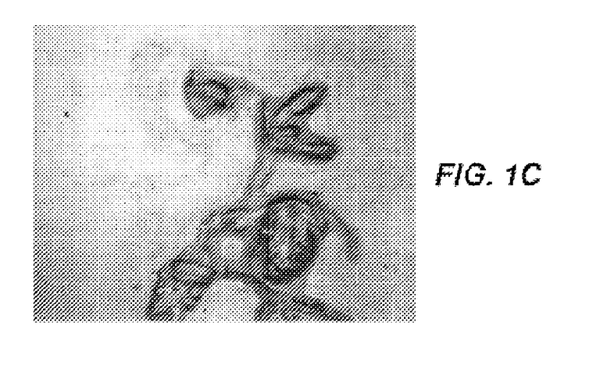
FIGS. 1c and 1d are reflectance micrographs showing the absence of a barrier layer on a surface after application of a control composition to the surface.
Figure 1D:
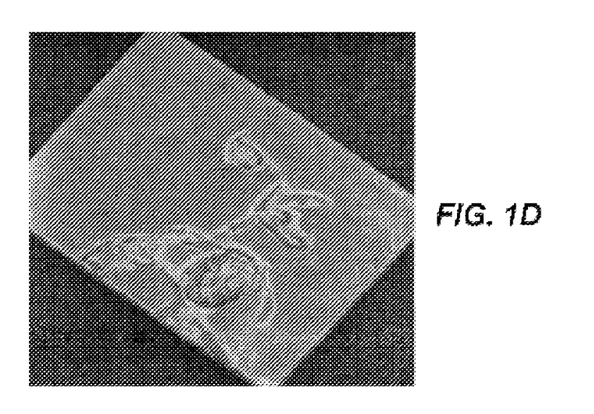

The term "essentially continuous film" means that a residue of the nonvolatile components of the composition in the form of a barrier layer is present on at least 50%, at least 60%, at least 70%, or at least 80%, preferably at least 85% or at least 90%, and more preferably at least 95%, of the area of the treated surface area. An "essentially continuous" film is demonstrated in the reflectance micrographs of the figures, which are discussed hereafter. The term "essentially continuous film" as used herein is synonymous with the term "essentially continuous layer", "barrier layer", and "barrier film".

An organic acid having a log P of less than one acts to control nonenveloped viruses. An organic acid having a log P of one or greater controls viruses and also imparts an antibacterial efficacy. A combination of a first organic acid having a log P less than one and a second organic acid having a log P of one or greater provides a control of nonenveloped viruses and Gram positive and Gram negative bacteria. The organic acid also controls influenza viruses.

Although liquid compositions containing an antimicrobial agent, like triclosan, have demonstrated a rapid and effective antibacterial activity against Gram positive and Gram negative bacteria, control of viruses has been inadequate. Virus control on skin and inanimate surfaces is very important in controlling the transmission of numerous viral-mediated diseases.

For example, rhinoviruses are the most significant microorganisms associated with the acute respiratory illness referred to as the "common cold." Other viruses, such as parainfluenza viruses, respiratory syncytial viruses (RSV), enteroviruses, and coronaviruses, also are known to cause symptoms of the "common cold," but rhinoviruses are theorized to cause the greatest number of common colds. Rhinoviruses also are among the most difficult of the cold-causing viruses to control, and have an ability to survive on a hard dry surface for more than four days. In addition, most viruses are inactivated upon exposure to a 70% ethanol solution. However, rhinoviruses remain viable upon exposure to ethanol.

Because rhinoviruses are the major known cause of the common cold, it is important that a composition having antiviral activity is active against the rhinovirus. Although the molecular biology of rhinoviruses is now understood, finding effective methods for preventing colds caused by rhinoviruses, and for preventing the spread of the virus to noninfected subjects, has been fruitless.

It is known that iodine is an effective antiviral agent, and provides a persistent antirhinoviral activity on skin. In experimentally induced and natural cold transmission studies, subjects who used iodine products had significantly fewer colds than placebo users. This indicates that iodine is effective for prolonged periods at blocking the transmission of rhinoviral infections. Thus, the development of products that deliver both immediate and persistent antiviral activity would be effective in reducing the incidence of colds. Likewise, a topically applied composition that exhibits antiviral activity would be effective in preventing and/or treating diseases caused by other nonenveloped viruses, including acid-labile viruses.

Rotavirus infection is an infection of the digestive tract, and is the most common cause of severe diarrhea among children, resulting in over 50,000 hospitalizations yearly in the U.S. alone. Rotaviral infections are particularly problematic in close communities, such as child care facilities, geriatric facilities, family homes, and children's hospitals.

The most common mode of transmitting rotavirus is person to person spread through contaminated hands, but transmission also can occur through ingestion of contaminated water or food, or through contact with contaminated surfaces. The rotavirus then enters the body through contact with the mouth.

It is known that washing hands and hard surfaces with soap and/or other cleansers does not kill rotavirus, but helps prevent its spread. An oral rotavirus vaccine has been approved for use in children in the U.S., but its use is not recommended because of a severe adverse side effect. Because no other effective way to eliminate rotavirus, or its spread, is currently available, workers in close communities, especially those catering to children, must adhere to strict hygienic practices to help curtail the spread of rotavirus. An improved composition having enhanced antiviral efficacy, including persistent antiviral efficacy, in inactivating rotaviruses would further curtail the spread of rotavirus infections.

Virucidal means capable of inactivating or destroying a virus. As used herein, the term "persistent antiviral efficacy" or "persistent antiviral activity" means leaving a residue or imparting a condition on animate (e.g., skin) or inanimate surfaces that provides significant antiviral activity for an extended time after application. In some embodiments, a "persistent antiviral efficacy" or "persistent antiviral activity" means leaving a barrier residue or film of antiviral agents, including organic acids, on animate (e.g., skin) or inanimate surfaces that provides significant antiviral activity for an extended time after application. The barrier residue or film can be continuous or essentially continuous, and resists removal from a treated surface during water rinsing.

A composition of the present invention provides a persistent antiviral efficacy, i.e., preferably a log reduction of at least 3, and more preferably a log reduction of at least log 4, against nonenveloped viruses, including acid-labile viruses, such as rhinovirus serotypes, within 30 seconds of contact with the composition. Antiviral activity is maintained for at least about 0.5 hour, preferably at least about one hour, and more preferably for at least about two hours, at least about three hours, or at least about four hours after contact with the composition. In some preferred embodiments, antiviral activity is maintained for about six to about eight hours after contact with the composition. In some embodiments, the persistent antiviral activity is attributed, at least in part, to the reservoir of organic acids present in the barrier layer or film of the composition on a treated surface. The methodology utilized to determine a persistent antiviral efficacy is discussed below.

To be efficacious against rhinovirus and other viruses, antiviral compositions are uniformly applied to the skin, e.g., an individual's hands, or to an inanimate surface. A uniform application can be accomplished using a lotion, spray, or similar liquid and gel product forms, but these methods all involve application of a composition in a wet state, thereby producing wet skin or a wet surface in the process. Various individuals, such as sensitive individuals or individuals requiring several applications of a composition each day, desire the benefit of antiviral efficacy without having wet hands, and thereby reducing the skin irritation potential of the composition.

The solid antiviral compositions of the present invention are highly effective in providing a rapid and persistent control of nonenveloped viruses and influenza viruses. The highly effective compositions comprise a powdered solid substrate, a virucidally effective amount of an organic acid, and optional ingredients. The solid compositions are surprisingly mild to the skin. Thus, mild and effective compositions that solve the problem of viral control are provided to consumers.

The present solid compositions provide an effective and persistent inactivation of nonenveloped viruses. Nonenveloped viruses include, but are not limited to, adenoviruses, papovaviruses, parvoviruses, astroviruses, caliciviruses (including Norwalk virus), rotoviruses (including rotavirus gastroenteritis), and picomaviruses (including rhinovirus, polio virus, and hepatitis A virus). The solid compositions also are effective against influenza viruses.

The solid antiviral compositions of the present invention are highly efficacious in household and institutional applications. The present compositions efficaciously and rapidly disinfect inanimate surfaces that are infected or contaminated with viruses (e.g., rhinoviruses and rotaviruses). The present compositions also provide a persistent antiviral effectiveness.

The present compositions can be used in vitro and in vivo. In vitro means in or on nonliving things, especially on inanimate objects having hard or soft surfaces located or used where preventing viral transmission is desired, most especially on objects that are touched by human hands. In vivo means in or on animate objects, especially on mammal skin, and particularly on hands.

As illustrated in the following nonlimiting embodiments, an antiviral composition of the present invention comprises: (a) a powdered solid substrate and (b) a virucidally effective amount of an organic acid. The solid compositions also can contain optional ingredients. The compositions preferably are capable of forming an essentially continuous film or layer of nonvolatile composition ingredients on a treated animate surface. The film or layer resists removal from the treated surface for several hours after application. In particular, an effective amount of composition ingredients remain on a treated surface after ten rinsings, and at least 50%, preferably at least 60%, and more preferably at least 70%, of the nonvolatile composition ingredients remains on a treated surface after three rinsings.

In embodiments wherein skin is treated, "rinsing" means gently rubbing treated skin for about 30 seconds under a moderate flow of tap water having a temperature of about 30° C. to about 40° C., then air-drying the skin.

The solid compositions further exhibit a log reduction against nonenveloped viruses, including acid-labile viruses, such as rhinovirus serotypes of about 5 after 30 seconds contact, and a log reduction against these acid-labile viruses of at least 3 about five hours after contact, and at least about 2 about six to about eight hours after contact. The compositions also are effective against influenza viruses, are mild to the skin, and it is not necessary to rinse or wipe the compositions from the skin.

In accordance with the invention, a present antiviral composition can further comprise additional optional ingredients disclosed hereafter, like active antibacterial agents, alcohols, glycols, vitamins, dyes, skin conditioners, and perfumes. The compositions typically are free of intentionally added cleansing surfactants, i.e., contain 0% to about 0.5%, by weight, of compounds that exhibit surface activity.

The following ingredients are present in an antimicrobial composition of the present invention.

A. Powdered Solid Substrate

A present solid composition contains about 80% to about 99.9%, by weight, of a powdered solid substrate. A powdered solid substrate comprises powdered particles of a substrate capable of absorbing, adsorbing, entrapping, or otherwise retaining at least its own weight in water, and typically several times its weight in water without exhibiting a "wet" feel. In general, the solid substrate is capable of retaining at least its own weight in water, and typically 2 to 25 times its weight in water, while maintaining a free-flowing property. The powdered solid substrate preferably is hydrated, i.e., comprises water in an amount up to the water retention capacity of the solid substrate. Additional optional composition components, such as an alcohol or a polyhydric alcohol, also can be added to the powdered solid substrate.

Although a present composition typically is a dry composition, when applied and rubbed on the skin or other surface, the composition liquefies by the release of water and other optional ingredients from the powdered substrate. Liquefaction helps provide a uniform application of the composition to the skin, and in some embodiments provides a continuous film of composition ingredients on treated skin, which in turn improves the persistent antiviral activity of the composition. A present composition is not necessarily a dry composition. Pastes and semisolids also are encompassed by the present invention.

The powdered solid substrate typically has an average particle size of about 1 to about 50, preferably about 2 to about 40, and more preferably 3 to about 35 nanometers (nm). The powdered solid substrate also can have a particle size distribution of about 0.01 to about 100, preferably about 0.02 to about 90, and more preferably about 0.03 to about 80 nm. These preferred average particle sizes and particle size distributions are such that individuals cannot feel the particles when they are rubbed into the skin, i.e., the powdered solid substrate does not have a sandy or grainy feel during application. When the powdered solid substrate comprises a clay or a superabsorbent polymer, the clay or superabsorbent polymer can have an average particle size in excess of 50 nm, e.g., up to 1 mm (millimeter).

The solid substrate typically is a low density, inorganic powder, and particularly a silica, like a fumed silica, such as AEROSIL® from DeGussa or Cab-O-Sil® from Cabot Corp. Often the solid substrate is hydrophilic. The solid substrate also can be hydrophobic and/or organic in nature, as disclosed in EP 1 386 599.

One powdered solid substrate is termed "dry water," or powdered water. Dry water or hydrated silica, is a silica-based substrate containing several times its weight in water. The preparation of a dry water is discussed, for example, in U.S. Pat. No. 3,393,155, EP 0 855 172, and EP 1 386 599, each incorporated herein by reference.

One powdered solid substrate useful in a present composition contains, by weight, 95% water and 5% of a silica, like AEROSIL® R18125 (i.e., silanamine, 1,1,1-trimethyl(triethylsilyl)) available from DeGussa. Other hydrophilic silica compounds also can be used to prepare dry water, e.g., trimethoxy siloxylated silicic acid anhydride. Dry water has an excellent ability to liquefy to a lotion when applied to and rubbed on a substrate, such as human skin.

Other powdered solid substrates also are useful in the present invention. For example, a class of polymers termed superabsorbent polymers are useful. Superabsorbent polymers typically are lightly-crosslinked, partially-neutralized polyacrylic acid polymers, capable of absorbing and retaining several times their weight of water.

Additional useful powdered solid substrates are the solid absorbents and adsorbents. As used herein, the term "absorbent" means solids that imbibe water and other compounds. Solids that attach water and other compounds to their surface are termed "adsorbents". Examples of solid absorbents and adsorbents include, but are not limited to, aluminum silicate, aluminum starch octenylsuccinate, calamine, calcium silicate, cellulose, chalk, corn starch, dextrin, diatomaceous earth, fullers earth, glyceryl starch, kaolin, magnesium aluminum silicate, magnesium carbonate, magnesium hydroxide, magnesium oxide, magnesium silicate, magnesium trisilicate, maltodextrin, microcrystalline cellulose, oat bran, oat flour, oatmeal, potassium aluminum polyacrylate, potato starch, rice starch, silica, talc, wheat starch, and mixtures thereof.

One particularly useful class of absorbents are the clays, both swelling and non-swelling. Swelling clays have the ability to absorb water and are swellable, layered organic materials. Suitable swelling clays include, but are not limited to, montmorillonite, saponite, nontronite, laponite, beidelite, hectorite, suconite, stevensite, vermiculite, volkonskoite, magadite, medmontite, kenyaite, and mixtures thereof.

Preferably, the swelling clay is a smectite or vermiculite clay. More preferably, the clay is a smectite clay. Examples of suitable smectites include, but are not limited to, montmorillonite (often referred to as bentonite), beidelite, nontronite, hectorite, saponite, sauconite, and laponite. Bentonite is a naturally occurring combination of clay particles, rich in montmorillonite and also including other smectites, as well as nonclay mineral constituents.

Suitable nonswelling clays include, without limitation, kaolin minerals (including kaolinite, dickite, and nacrite), serpentine minerals, mica minerals (including illite), chlorite minerals, sepolite, palygorskite, bauxite, and mixtures thereof.

The powdered, solid substrate is a dry, free-flowing powder. As discussed below, if desired, various composition ingredients can be dissolved or dispersed in water prior to adding water the powdered solid substrate, such that these ingredients also are incorporated into or onto the powdered solid substrate.

B. Organic Acid

A present solid antiviral composition also contains an organic acid in a sufficient amount to control and inactivate viruses on a surface contacted by the antiviral composition. The organic acid acts to provide a rapid control of viruses, and provides a persistent viral control.

In particular, an organic acid is present in the composition in a sufficient amount such that the pH of an animate surface contacted by the composition is lowered to degree wherein a persistent viral control is achieved. This persistent viral control is achieved regardless of whether the composition is rinsed from, or allowed to remain on, the contacted surface. The organic acid remains at least partially undissociated in the composition, and remains so during and after application to a surface.

Upon application to a surface, such as human skin, the pH of the surface is sufficiently lowered such that a persistent viral control is achieved. In preferred embodiments, a residual amount of the organic acid remains on the skin, even after a rinsing step, in order to impart a persistent viral control. However, even if the organic acid is essentially completely rinsed from the surface, the surface pH has been sufficiently lowered to impart a viral control for at least 0.5 hour.

A present composition is a leave-on composition, i.e., is not intended to be rinsed from the skin. However, after three rinsings, at least 50% of nonvolatile composition ingredients remain on the surface, and an effective amount of the composition remains on the treated surface after ten rinsings.

Typically, an organic acid is included in a present composition in an amount of about 0.05% to about 15%, and preferably about 0.1% to about 10%, by weight of the composition. To achieve the full advantage of the present invention, the organic acid is present in an amount of about 0.15% to about 6%, by weight of the composition. In preferred embodiments, a mixture of organic acids is included in the composition. The total amount of organic acid is related to the class of organic acid used, and to the identity of the specific acid or acids used.

An organic acid included in a present antiviral composition preferably does not penetrate the surface to which it is applied, e.g., remains on the skin surface as opposed to penetrating the skin, and forms a layer or film on the skin. The organic acid, therefore, preferably is a hydrophobic organic acid.

In one embodiment of the present invention, the organic acid has a log P of less than one, and preferably less than 0.75. To achieve the full advantage of the present invention, the organic acid has a log P of less than 0.5. In this embodiment, the organic acid acts to provide an effective and persistent viral control.

In another embodiment, the organic acid has a log P of 1 or greater, for example, 1 to about 100. In this embodiment, the organic acid effectively controls viruses.

It is envisioned that, by incorporating a first organic acid having a log P of less than one and a second organic acid having a log P of 1 or greater into a present composition, the first and second organic acids act to provide a persistent control of a wider spectrum viruses.

As used herein, the term "log P" is defined as the log of the water-octanol partition coefficient, i.e., the log of the ratio $P_W/P_O$, wherein $P_W$ is the concentration of an organic acid in water and $P_O$ is the concentration of the organic acid in octanol, at equilibrium and 25° C. The water-octanol coefficient can be determined by the U.S. Environmental Protection Agency Procedure, "OPPTS 830.7560 Partition Coefficient (n-Octanol/Water), Generator Column Method" (1996).

Organic acids having a log P less than one typically are water insoluble, e.g., have a water solubility of less than about 0.5 wt % at 25° C. Organic acids having a log P of one or greater typically are considered water soluble, e.g., have a water solubility of at least 0.5 wt %, at 25° C.

An organic acid useful in a present antiviral composition comprises a monocarboxylic acid, a polycarboxylic acid, a polymeric acid having a plurality of carboxylic, phosphate, sulfonate, and/or sulfate moieties, or mixtures thereof. In addition to acid moieties, the organic acid also can contain other moieties, for example, hydroxy groups and/or amino groups. In addition, an organic acid anhydride can be used in a composition of the present invention as the organic acid.

In one embodiment, the organic acid comprises a monocarboxylic acid having a structure $RCO_2H$, wherein R is $C_{1-6}$alkyl, hydroxy$C_{1-6}$alkyl, halo$C_{1-6}$alkyl, phenyl, or substituted phenyl. The alkyl groups can be substituted with phenyl groups and/or phenoxy groups, and these phenyl and phenoxy groups can be substituted or unsubstituted.

Nonlimiting examples of monocarboxylic acids useful in the present invention are acetic acid, propionic acid, hydroxyacetic acid, lactic acid, benzoic acid, phenylacetic acid, phenoxyacetic acid, zimanic acid, 2-, 3-, or 4-hydroxybenzoic acid, anilic acid, o-, m-, or p-chlorophenylacetic acid, o-, m-, or p-chlorophenoxyacetic acid, and mixtures thereof. Additional substituted benzoic acids are disclosed in U.S. Pat. No. 6,294,186, incorporated herein by reference. Examples of substituted benzoic acids include, but are not limited to, salicyclic acid, 2-nitrobenzoic acid, thiosalicyclic acid, 2,6-dihydroxybenzoic acid, 5-nitrosalicyclic acid, 5-bromosalicyclic acid, 5-iodosalicyclic acid, 5-fluorosalicylic acid, 3-chlorosalicylic acid, 4-chlorosalicyclic acid, and 5-chlorosalicyclic acid.

In another embodiment, the organic acid comprises a polycarboxylic acid. The polycarboxylic acid contains at least two, and up to four, carboxylic acid groups. The polycarboxylic acid also can contain hydroxy or amino groups, in addition to substituted and unsubstituted phenyl groups. Preferably, the polycarboxylic acid has a water solubility of at least about 0.05%, by weight, at 25° C.

Nonlimiting examples of polycarboxylic acids useful in the present invention include malonic acid, succinic acid, glutaric acid, adipic acid, terephthalic acid, phthalic acid, pimelic acid, suberic acid, azelaic acid, sebacic acid, fumaric acid, maleic acid, tartaric acid, malic acid, citric acid, maleic acid, aconitic acid, and mixtures thereof.

Anhydrides of polycarboxylic and monocarboxylic acids also are organic acids useful in the present compositions. Preferred anhydrides are anhydrides of polycarboxylic acids, e.g., phthalic anhydride. At least a portion of the anhydride is hydrolyzed to a carboxylic acid because of the pH of the composition. It is envisioned that an anhydride can be slowly hydrolyzed on a surface contacted by the composition, and thereby assist in providing a persistent antiviral activity.

In a third embodiment, the organic acid comprises a polymeric carboxylic acid, a polymeric sulfonic acid, a sulfated polymer, a polymeric phosphoric acid, or mixtures thereof. The polymeric acid has a molecular weight of about 500 g/mol to 10,000,000 g/mol, and includes homopolymers, copolymers, and mixtures thereof. The polymeric acid preferably is capable of forming a substantive film on a surface and has a glass transition temperature, $T_g$, of less than 25° C., preferably less than 20° C., and more preferably less than about 15° C. The glass transition temperature is the temperature at which an amorphous material, such as a polymer, changes from a brittle, vitreous state to a plastic state. The $T_g$ of a polymer is readily determined by persons skilled in the art using standard techniques.

The polymeric acids are uncrosslinked or only very minimally crosslinked. The polymeric acids typically are prepared from ethylenically unsaturated monomers having at least one hydrophilic moiety, such as carboxyl, carboxylic acid anhydride, sulfonic acid, and sulfate. The polymeric acid can contain a comonomer, such as styrene or an alkene, to increase the hydrophobicity of the polymeric acid.

Examples of monomers used to prepare the polymeric organic acid include, but are not limited to:

(a) Carboxyl group-containing monomers, e.g., monoethylenically unsaturated mono- or polycarboxylic acids, such as acrylic acid, methacrylic acid, maleic acid, fumaric acid, crotonic acid, sorbic acid, itaconic acid, ethacrylic acid, α-chloroacrylic acid, α-cyanoacrylic acid, β-methlacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, citraconic acid, mesaconic acid, glutaconic acid, aconitic acid, tricarboxyethylene, and cinnamic acid;

(b) Carboxylic acid anhydride group-containing monomers, e.g., monoethylenically unsaturated polycarboxylic acid anhydrides, such as maleic anhydride; and (c) Sulfonic acid group-containing monomers, e.g., aliphatic or aromatic vinyl sulfonic acids, such as vinylsulfonic acid, allylsulfonic acid, vinyltoluenesulfonic acid, styrenesulfonic acid, sulfoethyl (meth)acrylate, 2-acrylamido-2-methylpropane sulfonic acid, sulfopropyl (meth)acrylate, and 2-hydroxy-3-(meth)acryloxy propyl sulfonic acid.

The polymeric acid can contain other copolymerizable units, i.e., other monoethylenically unsaturated comonomers, well known in the art, as long as the polymer is substantially, i.e., at least 10%, and preferably at least 25%, acid group containing monomer units. To achieve the full advantage of the present invention, the polymeric acid contains at least 50%, and more preferably, at least 75%, and up to 100%, acid group containing monomer units. The other copolymerizable units, for example, can be styrene, an alkene, an alkyl acrylate, or an alkyl methacrylate. The polymeric acid also can be partially neutralized. However, a sufficient number of the acid groups remain unneutralized to reduce skin pH and impart a persistent antiviral activity.

A polymeric acid assists in forming a film or layer of residual organic acid on the skin, and assists further in forming a more continuous layer of residual organic acid on the skin. A polymeric acid typically is used in conjunction with a monocarboxylic acid and/or a polycarboxylic acid.

One preferred polymeric acid is a polyacrylic acid, either a homopolymer or a copolymer, for example, a copolymer of acrylic acid and an alkyl acrylate and/or alkyl methacrylate. Another preferred polymeric acid is a homopolymer or a copolymer of methacrylic acid.

Exemplary polymeric acids useful in the present invention include, but are not limited to:

|  |  |
|---|---|
| Carbomers | (CARBOPOL 910, 934, 934P, 940, 941, ETD 2050; ULTREZ 10, 21) (CARBOPOL ETD 2050) |
| Acrylates/C20-30 Alkyl Acrylate Crosspolymer | (ULTREZ 20) |
| Acrylates/Beheneth 25 Methacrylate Copolymer | (ACULYN 28) |
| Acrylates/Steareth 20 Methacrylate Copolymer | (ACULYN 22) |
| Acrylates/Steareth 20 Methacrylate Crosspolymer | (ACULYN 88) |
| Acrylates Copolymer | (CAPIGEL 98) |
| Acrylates Copolymer | (AVALURE AC) |
| Acrylates/Palmeth 25 Acrylate Copolymer | (SYNTHALEN 2000) |
| Ammonium Acrylate Copolymers | |
| Sodium Acrylate/Vinyl Alcohol Copolymer | |
| Sodium Polymethacrylate | |
| Acrylamidopropyltrimonium Chloride/Acrylates Copolymer | |
| Acrylates/Acrylamide Copolymer | |
| Acrylates/Ammonium Methacrylate Copolymer | |
| Acrylates/C10-30 Alkyl Acrylate Crosspolymer | |
| Acrylates/Diacetoneacrylamide Copolymer | |
| Acrylates/Octylacrylamide Copolymer | |
| Acrylates/VA Copolymer | |
| Acrylic Acid/Acrylonitrogens Copolymer | |

In a preferred embodiment of the present invention, the organic acid comprises one or more polycarboxylic acid, e.g., citric acid, malic acid, tartaric acid, or a mixture of any two or all three of these acids, and a polymeric acid containing a plurality of carboxyl groups, for example, homopolymers and copolymers of acrylic acid or methacrylic acid.

The organic acid typically is a solid, and can be blended with the powdered solid substrate to provide a mixture of the organic acid and powdered solid substrate. In this embodiment, the solid organic acid preferably has a sufficiently small particle size such that it cannot be felt during, or after, application to the skin. Alternatively, the organic acid can be dissolved or dispersed in water or other composition ingredients, and added to the solid substrate or a hydrated solid substrate to be incorporated into (e.g., absorbed) or onto (e.g., adsorbed) the solid substrate.

C. Optional Ingredients

An antiviral composition of the present invention also can contain optional ingredients well known to persons skilled in the art. The particular optional ingredients and amounts that can be present in the composition are discussed hereafter.

The optional ingredients are present in a sufficient amount to perform their intended function and not adversely affect the antiviral efficacy of the composition, and in particular not adversely affect the antiviral effect provided by the organic acid. Optional ingredients typically are present, individually or collectively, from 0% to about 20%, by weight of the composition.

Classes of optional ingredients include, but are not limited to, alcohols, active antibacterial agents, dyes, fragrances, pH adjusters, skin conditioners, emollients, preservatives, buffering agents, antioxidants, vitamins, chelating agents, and similar classes of optional ingredients known to persons skilled in the art.

Solid antiviral compositions of the present invention can contain, if at all, about 0.1% to about 60%, by weight, of an alcohol containing one to six carbon atoms, i.e., a $C_{1-6}$ alcohol. Suitable alcohols include, but are not limited to, methanol, ethanol, propanol, and isopropyl alcohol. An alcohol is added in a sufficient amount to serve its intended function, e.g., dissolve the organic acid or provide an antiviral and/or antibacterial effect.

Solid antiviral compositions of the present invention also can contain an active antibacterial agent to provide or enhance antibacterial activity of the composition. Several different classes of active antibacterial agents can be used. Examples of antibacterial agents include a bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and triclosan (i.e., 2,4,4'-trichloro-2'-hydroxydiphenylether).

In particular, an antibacterial agent can be present, if at all, in an amount of 0.1% to about 5%, and preferably about 0.1% to about 2%, and more preferably, about 0.3% to about 1%, by weight of the composition.

Preferred antibacterial agents useful in the present invention are exemplified by the following classes of compounds used alone or in combination:

(1) Phenolic antibacterial agents (a) 2-Hydroxydiphenyl Compounds wherein Y is chlorine or bromine, Z is $SO_3H$, $NO_2$, or $C_1$-$C_4$ alkyl, r is 0 to 3, o is 0 to 3, p is 0 or 1, m is 0 or 1, and n is 0 or 1.

In preferred embodiments, Y is chlorine or bromine, m is 0, n is 0 or 1, o is 1 or 2, r is 1 or 2, and p is 0.

In especially preferred embodiments, Y is chlorine, m is 0, n is 0, o is 1, r is 2, and p is 0.

A particularly useful 2-hydroxydiphenyl compound has a structure:

having the adopted name, triclosan, and available commercially under the tradename IRGASAN DP300, from Ciba Specialty Chemicals Corp., Greensboro, N.C. Another useful 2-hydroxydiphenyl compound is 2,2'-dihydroxy-5,5'-dibromo-diphenyl ether.

(b) Phenol Derivatives wherein $R_1$ is hydro, hydroxy, $C_1$-$C_4$ alkyl, chloro, nitro, phenyl, or benzyl; $R_2$ is hydro, hydroxy, $C_1$-$C_6$ alkyl, or halo; $R_3$ is hydro, $C_1$-$C_6$ alkyl, hydroxy, chloro, nitro, or a sulfur in the form of an alkali metal salt or ammonium salt; $R_4$ is hydro or methyl; and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in U.S. Pat. No. 6,436,885, incorporated herein by reference.

(c) Diphenyl Compounds wherein X is sulfur or a methylene group, $R_6$ and $R'_6$ are hydroxy, and $R_7$, $R'_7$, $R_8$, $R'_8$, $R_9$, $R'_9$, $R_{10}$, and $R'_{10}$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine. Other diphenyl compounds are listed in U.S. Pat. No. 6,436,885, incorporated herein by reference.

(2) Quaternary Ammonium Antibacterial Agents

Useful quaternary ammonium antibacterial agents have a general structural formula:

wherein at least one of $R_{11}$, $R_{12}$, $R_{13}$, and $R_{14}$ is an alkyl, aryl, or alkaryl substituent containing 6 to 26 carbon atoms. Alternatively, any two of the R substituents can be taken together, with the nitrogen atom, to form a five- or six-membered aliphatic or aromatic ring. Preferably, the entire ammonium cation portion of the antibacterial agent has a molecular weight of at least 165.

The substituents $R_{11}$, $R_{12}$, $R_{13}$, and $R_{14}$ can be straight chained or can be branched, but preferably are straight chained, and can include one or more amide, ether, or ester linkage. In particular, at least one substituent is $C_6$-$C_{26}$alkyl, $C_6$-$C_{26}$alkoxyaryl, $C_6$-$C_{26}$alkaryl, halogen-substituted $C_6$-$C_{26}$alkaryl, $C_6$-$C_{26}$alkylphenoxyalkyl, and the like. The remaining substituents on the quaternary nitrogen atom other than the above-mentioned substituent typically contain no more than 12 carbon atoms. In addition, the nitrogen atom of the quaternary ammonium antibacterial agent can be present in a ring system, either aliphatic, e.g., piperdinyl, or aromatic, e.g., pyridinyl. The anion X can be any salt-forming anion which renders the quaternary ammonium compound water soluble. Anions include, but are not limited to, a halide, for example, chloride, bromide, or iodide, methosulfate, and ethosulfate.

Preferred quaternary ammonium antibacterial agents have a structural formula:

wherein $R_{12}$ and $R_{13}$, independently, are $C_8$-$C_{12}$alkyl, or $R_{12}$ is $C_{12}$-$C_{16}$alkyl, $C_8$-$C_{18}$alkylethoxy, or $C_8$-$C_{18}$alkylphenylethoxy, and $R_{13}$ is benzyl, and X is halo, methosulfate, ethosulfate, or p-toluenesulfonate. The alkyl groups $R_{12}$ and $R_{13}$ can be straight chained or branched, and preferably are linear.

The quaternary ammonium antibacterial agent in a present composition can be a single quaternary ammonium compound, or a mixture of two or more quaternary ammonium compounds. Particularly useful quaternary ammonium antibacterial agents include dialkyl($C_8$-$C_{10}$) dimethyl ammonium chlorides (e.g., dioctyl dimethyl ammonium chloride), alkyl dimethyl benzyl ammonium chlorides (e.g., benzalkonium chloride and myristyl dimethylbenzyl ammonium chloride), alkyl methyl dodecyl benzyl ammonium chloride, methyl dodecyl xylene-bis-trimethyl ammonium chloride, benzethonium chloride, dialkyl methyl benzyl ammonium chloride, alkyl dimethyl ethyl ammonium bromide, and an alkyl tertiary amine. Polymeric quaternary ammonium compounds based on these monomeric structures also can be used in the present invention. One example of a polymeric quaternary ammonium compound is POLYQUAT®, e.g., a 2-butenyl dimethyl ammonium chloride polymer. The above quaternary ammonium compounds are available commercially under the tradenames BARDAC®, BTC®, HYAMINE®, BARQUAT®, and LONZABAC®, from suppliers such as Lonza, Inc., Fairlawn, N.J. and Stepan Co., Northfield, Ill.

Additional examples of quaternary ammonium antibacterial agents include, but are not limited to, alkyl ammonium halides, such as cetyl trimethyl ammonium bromide; alkyl aryl ammonium halides, such as octadecyl dimethyl benzyl ammonium bromide; N-alkyl pyridinium halides, such as N-cetyl pyridinium bromide; and the like. Other suitable quaternary ammonium antibacterial agents have amide, ether, or ester moieties, such as octylphenoxyethoxy ethyl dimethyl benzyl ammonium chloride, N-(laurylcocoaminoformylmethyl)pyridinium chloride, and the like. Other classes of quaternary ammonium antibacterial agents include those containing a substituted aromatic nucleus, for example, lauryloxyphenyl trimethyl ammonium chloride, cetylaminophenyl trimethyl ammonium methosulfate, dodecylphenyl trimethyl ammonium methosulfate, dodecylbenzyl trimethyl ammonium chloride, chlorinated dodecylbenzyl trimethyl ammonium chloride, and the like.

Specific quaternary ammonium antibacterial agents include, but are not limited to, behenalkonium chloride, cetalkonium chloride, cetarylalkonium bromide, cetrimonium tosylate, cetyl pyridinium chloride, lauralkonium bromide, lauralkonium chloride, lapyrium chloride, lauryl pyridinium chloride, myristalkonium chloride, olealkonium chloride, and isostearyl ethyldimonium chloride. Preferred quaternary ammonium antibacterial agents include benzalkonium chloride, benzethonium chloride, cetyl pyridinium bromide, and methylbenzethonium chloride.

(3) Anilide and Bisguanidine Antibacterial Agents

Useful anilide and bisguanadine antibacterial agents include, but are not limited to, triclocarban, carbanilide, salicylanilide, tribromosalan, tetrachlorosalicylanilide, fluorosalan, chlorhexidine gluconate, chlorhexidine hydrochloride, and mixtures thereof.

Other specific classes of optional ingredients include inorganic phosphates, sulfates, and carbonates as buffering agents; EDTA and phosphates as chelating agents; and acids and bases as pH adjusters.

D. pH

The measurable pH of a present antiviral composition is less than about 5, and preferably less than about 4.5, at 25° C. The pH is measured after one gram of the composition is dispersed in 100 grams of water. To achieve the full advantage of the present invention, the pH is less than about 4. Typically, the pH of a present composition is about 2 to less than about 5, and preferably about 2.5 to about 4.5.

The pH of the composition is sufficiently low such that at least a portion of the organic acid is in the protonated form. The organic acid then has the capability of lowering surface pH, such as skin pH, to provide an effective viral control, without irritating the skin. The organic acid also deposits on the skin, preferably to form a layer or film, and resists removal by rinsing, to provide a persistent antiviral effect.

To demonstrate the new and unexpected results provided by the solid antiviral compositions of the present invention, the following example was prepared, and the ability of the composition to control rhinovirus, was determined. The weight percentage listed in the following example represents the actual, or active, weight amount of each ingredient present in the composition. The composition is prepared by blending the ingredients, as understood by those skilled in the art and as described below.

The following method was used as an antiviral residual efficacy test:

References: S. A. Sattar, *Standard Test Method for Determining the Virus-Eliminating Effectiveness of Liquid Hygienic Handwash Agents Using the Fingerpads of Adult Volunteers*, Annual Book of ASTM Standards. Designation E1838-96, incorporated herein by reference in its entirety, and referred to as "Sattar I"; and S. A. Sattar et al., *Chemical Disinfection to Interrupt Transfer of Rhinovirus Type 14 from Environmental Surfaces to Hands*, Applied and Environmental Microbiology, Vol. 59, No. 5, May, 1993, pp. 1579-1585, incorporated herein by reference in its entirety, and referred to as "Sattar II."

The method used to determine the Antiviral Index of the present invention is a modification of that described in Sattar I, a test for the virucidal activity of liquid hand washes (rinse-off products). The method is modified in this case to provide reliable data for leave-on products.

Modifications of Sattar I include the product being delivered directly to the skin as described below, virus inoculation of the fingerpads as described below, and viral recovery using ten-cycle washing. The inoculated skin site then is completely decontaminated by treating the area with 70% dilution of ethanol in water.

Procedure:

Ten-minute Test:

Subjects (5 per test product) initially wash their hands with a nonmedicated soap, rinse the hands, and allow the hands to dry.

The hands then are treated with 70% ethanol and air dried.

Test product (1.0 ml) is applied to the hands, except for the thumbs, and allowed to dry.

About 10 minutes (±30 seconds) after product application, 10 µl of a Rhinovirus 14 suspension (ATCC VR-284, approximately $1 \times 10^6$ PFU (plaque-forming units)/ml) is topically applied using a micropipette to various sites on the hand within a designated skin surface area known as fingerpads. At this time, a solution of rhinovirus also is applied to the untreated thumb in a similar manner.

After a dry-down period of 7-10 minutes, the virus then is eluted from each of the various skin sites with 1 ml of eluent (Earle's Balanced Salt Solution (EBSS) with 25% Fetal Bovine Serum (FBS)+1% pen-strep-glutamate), washing 10 times per site.

The inoculated skin site then is completely decontaminated by rinsing the area with 70% ethanol. Viral titers are determined using standard techniques, i.e., plaque assays or $TCID_{50}$ (Tissue Culture Infectious Dose).

One-hour test:

Subjects are allowed to resume normal activities (with the exception of washing their hands) between the 1-hour and 3-hour timepoints. After one hour, a rhinovirus suspension is applied to and eluted from designated sites on the fingerpads exactly as described in above for the 10-minute test.

EXAMPLE 1

The following composition was prepared:

| | |
|---|---|
| Dry water | 95.68% (by weight) |
| Citric acid | 2.16% |
| Malic acid | 2.16% |

The dry water contained 95% water and 5% AEROSIL® R18125 (silanamine, 1,1,1-trimethyl(triethylsilyl)). The antiviral composition was a dry, free-flowing powder. The composition was applied to the hands uniformly to provide an antiviral efficacy.

EXAMPLE 2

This example demonstrates the effect of a present powdered antiviral composition on skin pH.

Compositions A-D had the following formulations, and were prepared using the following procedure.

| Ingredient | | | Weight % "as is" | | | |
|---|---|---|---|---|---|---|
| Name | CTFA Name | Supplier | A | B | C | D |
| Deionized Water | Water | | 90.98 | 84.95 | 86.85 | 88.48 |
| Citric Acid | Citric Acid | Jungbunzlauer | 2.01 | 5.07 | 2.08 | 2.06 |
| dL-Malic Acid | Malic Acid | Spectrum | 2.02 | 4.99 | 2.06 | 2.00 |

-continued

| Ingredient | | | Weight % "as is" | | | |
|---|---|---|---|---|---|---|
| Name | CTFA Name | Supplier | A | B | C | D |
| Aerosil R812S | Silica Silylate | Degussa | 4.99 | 4.99 | 4.98 | 4.99 |
| Glycerin | Glycerin | | | | 1.03 | 1.41 |
| Isopropyl Palmitate | Isopropyl Palmitate | Rita | | | 1.00 | |
| DC Q7-9120 | Dimethicone | Dow Corning | | | 1.00 | |
| Cetyl Alcohol | Cetyl Alcohol | Cognis | | | 1.00 | |
| ULTREZ 10 NF | Carbomer | Noveon | | | | 1.06 |
| Total | | | 100.00 | 100.00 | 100.00 | 100.00 |

All compositions were dry, free flowing powders. All compositions were made using a Waring Blender and stored in a glass jar. Compositions A and B were prepared by dispersing the acids in water, adding the silica silylate, then blending at high speed for about 30 seconds.

Composition C was prepared by dispersing the acids in water, adding glycerin and isopropyl palmitate, then mixing briefly. In a separate beaker, cetyl alcohol and DC Q7-9120 was added and mixed until uniform. Silica silylate was added to the main batch, and mixed at high for about 25 seconds. Then, the cetyl alcohol/DC Q7-9120 blend was added, and the resulting mixture was mixed for an additional 10 seconds.

Composition D was prepared by dispersing the acids in water, adding glycerin, then mixing briefly. ULTREZ 10 was added and allowed to sit for about 5 minutes. Silica silylate was added and mixed for about 15 seconds. The sides of the blender were scraped, then the mixture was mixed again for about 30 seconds. The product was spread in a layer on aluminum foil to dry overnight, then crushed to a powder, and stored.

In this test, hands were washed with a mild soap (Johnson and Johnson Head-To-Toe Baby Wash), then dried with a paper towel. Baseline pH readings of the fingerpads were taken. Then, one or two grams of a powdered test composition powder (Compositions A-D) was placed in the palm of each hand. The powder was allowed to contact the hand for one minute, then initial skin pH readings were taken. Additional skin pH readings were taken at 15 minutes, 30 minutes, 1 hour, and 2 hours after application of the powdered composition. All compositions initially reduced the skin pH to below 4. Composition A maintained skin pH below 4 for 2 hours, wherein compositions B and C maintained the skin pH below 4 for 1 hour. The pH of skin treated with composition D was above pH 4 after 15 minutes.

| | Skin pH | | | |
|---|---|---|---|---|
| Time | A | B | C | D |
| Baseline | 5.49 | 5.60 | 5.35 | 5.59 |
| T = 0 | 3.36 | 2.73 | 2.94 | 3.74 |
| T = 15 min. | 3.62 | 3.43 | 3.47 | 4.36 |
| T = 30 min. | 3.73 | 3.78 | 3.72 | 4.36 |
| T = 1 hr. | 3.88 | 3.97 | 3.91 | 4.39 |
| T = 2 hrs. | 3.98 | 4.27 | 4.12 | 4.73 |

The following illustrates that polymeric acids, and especially an acrylic acid homopolymer or copolymer, impart antiviral efficacy. The polymeric acids have a low pH and good substantivity to skin, which effectively maintains a low skin pH over time, and helps provide a persistent antiviral efficacy. The polymeric acids also help provide an essentially continuous layer or film of an organic acid on treated surfaces, which in turn enhances the persistent antiviral activity of the composition.

A rapid and persistent antiviral activity also is demonstrated when an acrylic acid-based polymer is used in conjunction with polycarboxylic acids. It has been found that utilizing a low amount of a polymeric acid (e.g., about 0.1% to about 2%, by weight) together with a polycarboxylic acid, like citric acid, malic acid, tartaric acid, and mixtures thereof, enhances the antiviral activities of the polycarboxylic acids. This effect allows a reduction in the polycarboxylic acid concentration in an antiviral composition, without a concomitant decrease in antiviral efficacy. This reduction in polycarboxylic acid concentration improves composition mildness by reducing the irritation potential of the composition. It is theorized, but not relied upon herein, that the polymeric acid assists in forming a residual barrier film or layer of organic acids on a treated surface, which enhance the persistent antiviral activity of the composition.

The following tests demonstrate that a composition of the present invention provides an essentially continuous barrier layer of organic acid on a treated surface. In particular, the following tests show that a present composition resists rinsing from a treated surface, e.g., at least 50% of the nonvolatile composition ingredients (including the organic acid) remains on a treated surface after three rinsings, as determined from NMR and IR spectra. In addition, an effective antiviral amount of the nonvolatile composition ingredients remains on a treated surface after 10 rinsings, also determined using NMR and IR spectra.

In the following tests, an aqueous composition containing, by weight, 2% malic acid, 2% citric acid, 1% polyacrylic acid, 62% ethanol, and 0.5% hydroxyethylcellulose as a gelling agent (Composition A) was compared to an aqueous composition, containing 2% malic acid, 2% citric acid, and 62% ethanol (Composition B). The compositions were applied to a glass surface to provide a film. From infrared (IR) and nuclear magnetic resonance (NMR) spectra of the film taken after each rinse, it was determined that Composition B was completely rinsed from the surface after one rinsing with water. Composition B therefore failed to exhibit water resistance and failed to provide a film or layer of nonvolatile composition ingredients on the surface.

In contrast, IR and NMR spectra showed that Composition A provided a rinse-resistant film or layer of composition ingredients on the treated surface. The amount of composition ingredients that remained on the treated surface was reduced over the first three rinsings, then resisted further removal from the treated surface in subsequent rinses. The IR and NMR spectra showed that detectable and effective amounts of the nonvolatile composition ingredients remained on the treated surface after 10 water rinses.

Another test was performed to measure the contact angle of water on a surface. "Contact angle" is a measure of the wetting ability of water on a surface. In this test, Compositions A and B were applied to a glass surface and allowed to dry. Contact angle then was measured for glass treated with Compositions A and B, both unrinsed and rinsed, using deionized water. The contact angle of bare, i.e., untreated, glass also was measured as a control. The following table summarizes the results of the contact angle test.

|  | Composition A Unrinsed | Composition A Rinsed | Composition B Unrinsed | Composition B Rinsed | Bare Glass |
| --- | --- | --- | --- | --- | --- |
| Avg Reading (degrees) | 45.96 | 72.66 | 6.69 | 41.51 | 38.47 |
| Change in degrees |  | 26.7 |  | 34.8 |  |
| % Change |  | 58.1 |  | 520.2 |  |

The contact angle data shows that Composition A modifies the glass surface and provides a persistent barrier film or layer on the glass surface. The data also shows that Composition B is rinsed from the surface because the contact angle after rinsing of Composition B is essentially the same as that of bare glass.

Another test was performed to demonstrate metal ion uptake by a residual film of Composition A. In this test, films of Composition A were formed on glass, dried at least 4 hours, then exposed to solutions having a 0.5 M concentration of metal ions. Samples then were analyzed by SEM scan. The data in the following table shows that a film resulting from Composition A effectively binds several types of metal ions. It is theorized, but not relied upon, that this is a surface phenomenon because no mechanism for transporting metal ions into the film is known.

| Composition A Films on Glass (Metal-Soaked & Deionized Water Rinsed) (unless otherwise specified) | | |
| --- | --- | --- |
| Soaking Solution | EDS atomic % | EDS wt % |
| 0.56 wt % $CaCl_2$ in formula on 316 SS-No Rinse | 0.63% Ca | 1.71% Ca |
| 0.1 M Ca on 316 SS | 0.13% Ca | 0.21% Ca |
| 0.5 M Ca on 316 SS | 0.34% Ca | 0.54% Ca |
| 0.5 M Ca w/ more rinsing on 316 SS | 0.07% Ca | 0.12% Ca |
| 0.5 M Cu on 316 SS | 0.65% Cu | 1.59% Cu |
| 0.5 M Fe on Al 6061 | 0.41% Fe | 1.14% Fe |
| 0.5 M Zn on Al 6061 Metal Coupon anzlysis | 0.24% Zn | 0.90% Zn |
| DI water on 316 SS Fe compensated for in above datum | 0% Ca, 0% Cu, 0% Zn | 0% Ca, 0% Cu, 0% Zn |
| DI water on Al 6061 | 0.07% Ca, 0.08% Fe, 0.03% Cu [from Al] | 0.18% Ca, 0.29% Fe, 0.11% Cu [from Al] |

Reflectance micrographs showing the surface coverage of Compositions A and B also were taken (FIG. 1). The attached micrographs show that Composition A provides an essentially complete surface coverage, i.e., a more even coverage of Composition A on a treated surface, which provides an essentially continuous layer or film of nonvolatile composition ingredients on the surface. The attached micrographs are a digital conversion of reflectance values, which provide a direct correlation to surface coverage. The micrographs demonstrate that Composition A (FIGS. 1a) and 1b)) provides a film having improved adhesion, dispersion, and crystal formation compared to Composition B (FIGS. 1c) and 1d)).

The solid antiviral compositions of the present invention have several practical end uses, including antiseptics, disinfectants, hand sanitizers, deodorants, and similar personal care products. The compositions further can be used as an antiviral for inanimate surfaces, for example, sinks and countertops in healthcare facilities, food service areas, and food processing plants.

A solid antiviral composition of the present invention can be formulated into a variety of product forms, including powder, flake, granule, cylinder, tablet, pellet, lozenge, puck, briquette, brick, solid block, compressed sheet, unit dose, or a similar solid product form known in the art. A present solid composition also can be in the form of a paste or semisolid. The present solid compositions can be manufactured as dilute ready-to-use compositions, or as concentrates that are diluted prior to use.

One particular product form is a solid composition disposed within a water-soluble packet. The packet is added to a proper amount of water, and the composition is released when the packet dissolves. The water used as a solvent can contain additional ingredients, e.g., $C_{1-6}$ alcohols and surfactants, including anionic, cationic, nonionic, and ampholytic surfactants.

The water-soluble packet typically comprises a polyvinylalcohol. One form of water-soluble packet is disclosed in U.S. Pat. No. 5,316,688, incorporated herein by reference. Numerous other water-soluble packets are known to person skilled in the art, for example, in U.S. Pat. Nos. 5,070,126; 6,608,121; and 6,787,512; U.S. Patent Publication No. 2002/0182348; WO 01/79417; and European Patent Nos. 0 444 230, 1 158 016, 1 180 536, and 1 251 147, each incorporated herein by reference. Capsules are another related and useful product form.

Another useful product form is a stable, solid block that can be added to water to provide a liquid composition for practicing the present methods. The block can be tablet, briquette, puck, or larger solid block, e.g., the block can weigh from less than one ounce to several pounds, depending on the end use application. Such blocks generally comprise a binding agent. One stable block is disclosed in U.S. Pat. No. 6,432,906, incorporated herein by reference. As with the water-soluble packet, the water can contain additional ingredients to provide a desired benefit, i.e., a cleansing surfactant and/or additional $C_{1-6}$ alcohols for enhanced antiviral activity.

Still another product form is a web material or swab containing a powdered antiviral composition of the present invention. The composition then can be applied to the skin, or an inanimate surface, by wiping the surface with the web material containing the composition.

Another product form is an article, such as latex gloves, having the solid antiviral composition applied to, or imbedded into, the article. During use, the composition imparts an antiviral activity to the article itself and/or to a surface contacted by the article. Additional articles that can have a solid antiviral composition imbedded therein are plastic cups, food wraps, and plastic containers.

As discussed above, both animate and inanimate surfaces can be treated in accordance with the method of the present invention. A particularly important surface is mammalian skin, and especially human skin, to inactivate and interrupt the transmission of bacteria and viruses. However, the present method also is useful in treating other animate surfaces and inanimate surfaces of all types. The animate and inanimate surfaces can be treated with a solid antiviral composition of the present invention, or a solution or dispersion of the solid composition in an aqueous medium, comprising water only or additional ingredients well known in the cleansing and disinfecting arts.

The present method is useful to treat inanimate surfaces, both soft and hard. As used herein, the term "hard" refers to surfaces comprising refractory materials, such as glazed and unglazed tile, brick, porcelain, ceramics, metals, glass, and the like, and also includes wood and hard plastics, such as formica, polystyrenes, vinyls, acrylics, polyesters, and the like. A hard surface can be porous or nonporous. Methods of disinfecting hard surfaces are described in greater detail in U.S. Pat. Nos. 5,200,189; 5,314,687; and 5,718,910, each disclosure incorporated herein by reference.

The present method can be used to treat hard surfaces in processing facilities (such as dairy, brewing, and food processing facilities), healthcare facilities (such as hospitals, clinics, surgical centers, dental offices, and laboratories), long-term healthcare facilities (such as nursing homes), farms, cruise ships, hotels, airplanes, schools, and private homes.

The present method can be used to treat environmental surfaces such as floors, walls, ceilings, and drains. The method can be used to treat equipment such as food processing equipment, dairy processing equipment, brewery equipment, and the like. The compositions can be used to treat a variety of surfaces including food contact surfaces in food, dairy, and brewing facilities, such as countertops, furniture, sinks, and the like. The method further can be used to treat tools and instruments, such as medical tools and instruments, dental tools and instruments, as well as equipment used in the healthcare industries and institutional kitchens, e.g., knives, forks, spoons, wares (such as pots, pans, and dishes), cutting equipment, and the like.

Treatable inanimate surfaces include, but are not limited to, exposed environmental surfaces, such as tables, floors, walls, kitchenware (including pots, pans, knives, forks, spoons, plates), food cooking and preparation surfaces, including dishes and food preparation equipment, tanks, vats, lines, pumps, hoses, and other process equipment. One useful application of the composition is to dairy processing equipment, which is commonly made from glass or stainless steel. Dairy process equipment can be found in dairy farm installations and in dairy plant installations for the processing of milk, cheese, ice cream, and other dairy products.

The compositions also can be employed to coat or otherwise treat materials such as sponges, fibrous or nonfibrous web materials, swabs, flexible plastics, textiles, wood, and the like. Generally, the coating process is used to impart prolonged antiviral properties to a porous or nonporous surface by coating said surface with the composition.

The method of the present invention is useful in the treatment of medical carts, medical cages, and other medical instruments, devices, and equipment. Examples of medical apparatus treatable by the present method are disclosed in U.S. Pat. No. 6,632,291, incorporated herein by reference. The present method also is useful in treating utensil and chairs present in barber shops, and hair and nail salons. A further useful application is to treat coins, paper money, tokens, poker chips, and similar articles that are repeatedly handled by numerous individuals and can transmit viruses between individuals.

In addition to hard surfaces, the method also can be used to treat soft inanimate surfaces, like textiles, such as clothing, protective clothing, laboratory clothing, surgical clothing, patient clothing, carpets, bedding, towels, linens, and the like. The method also can be used to treat face masks, medical gowns, gloves, and related apparel utilized by medical and dental personnel.

Typically, the solid antiviral composition, alone or as a component of a composition, is applied to, optionally rubbed onto, the skin, and particularly, the hands. In one embodiment, the solid antiviral composition is applied to the nose and surrounding facial area, including the nasal mucosa, to provide a persistent antiviral activity. In this embodiment, the transmission of viruses present on the finger to the nasal mucosa is interrupted.

The term "nose and surrounding area" means the external portions of the nose, including the infratip lobule, columella, alar sidewalls, facets (or soft tissue triangles), the nostril sill, the colomella-labial angle or junction, the alar-facial groove or junction, the tip defining points, and other facial skin surrounding the nose, such as the skin between the upper lip extending to and above the nasal opening, and the cheek area near the nose. The term also includes the internal surfaces of the nose, including the nasal cavities up to the sinuses.

The solid composition can be applied to the nose and surrounding area by hand or can be sniffed into the nasal cavity. The solid composition also can be applied to the nose and surrounding area by a device designed to apply a dose, metered or unmetered, to the nasal cavity. The solid antiviral composition also can be incorporated into a web material or a swab for application to the skin or nasal passages.

The present invention also encompasses applying an effective amount of an antiviral composition of the present invention onto inanimate surfaces, such as household surfaces, e.g., countertops, kitchen surfaces, food preparing surfaces (cutting boards, dishes, pots and pans, and the like); major household appliances, e.g., refrigerators, freezers, washing machines, automatic dryers, ovens, microwave ovens, and dishwashers; cabinets; walls; floors; bathroom surfaces, shower curtains, garbage cans, and/or recycling bins, and the like. The present compositions also are useful on cruise ships, nursing homes, schools, and government and other public buildings, for example, to inhibit the transmission of viruses.

For household applications, hand-operated pump-type or pressurized aerosol sprayers can be used. The compositions also can be employed to coat or otherwise treat materials such as sponges, fibrous or nonfibrous web materials, swabs, flexible plastics, textiles, wood, and the like. Generally, the coating process is used to impart prolonged antiviral properties to a hard porous or nonporous surface by coating said surface with the composition. The compositions also can be incorporated into a web material to provide an antimicrobial wiping article. The wiping article can be used to sanitize animate or inanimate surfaces.

In yet another embodiment, a present solid composition can be added to water or an aqueous composition, thereby releasing the ingredients from the powdered solid substrate. The resulting solution can be applied to animate and inanimate surfaces to efficaciously sanitize animate and inanimate surfaces.

In one embodiment of the present invention, a person who either (a) is suffering from a rhinovirus cold, or is likely to be exposed to other individuals suffering from rhinovirus colds, or (b) is suffering from a rotaviral infection, or is likely to be exposed to other individuals suffering from a rotaviral infection, can apply a present antiviral composition to his or her hands. This application kills and inactivates rhinoviruses, rotaviruses, other nonenveloped virus particles present on the hands. The application also is effective against influenza viruses and noroviruses. The applied composition, allowed to remain on the treated skin, provides a persistent antiviral activity. Viruses, like rhinovirus and rotavirus particles, therefore, are not transmitted to noninfected individuals via hand-to-hand transmission. The amount of the composition applied, the frequency of application, and the period of use will vary depending upon the level of disinfection desired, e.g., the degree of microbial contamination and/or skin soiling. Typically, the composition is applied multiple times over a twenty-four hour period.

The present antimicrobial compositions provide the advantages of a broad spectrum viral control, in short contact times. The composition also imparts a persistent antiviral activity to the contacted surface and is nonirritating. A persistent antiviral activity is enhanced because a residual barrier layer or film of composition ingredients can remain on the skin.

Obviously, many modifications and variations of the invention as hereinbefore set forth can be made without departing from the spirit and scope thereof, and, therefore, only such limitations should be imposed as are indicated by the appended claims.

What is claimed is:

1. A method of reducing a virus population on a surface comprising contacting the surface with a solid composition comprising:
   a) a powdered solid substrate; and
   b) a virucidally effective amount of an organic acid comprising (i) two or more polycarboxylic acids selected from the group consisting of malonic acid, succinic acid, glutaric acid, adipic acid, pimelic acid, suberic acid, azelaic acid, sebacic acid, fumaric acid, maleic acid, tartaric acid, malic acid, maleic acid, citric acid, aconitic acid, and mixtures thereof, and (ii) a water soluble or water dispersible polymeric acid is selected from the group consisting of a polymeric carboxylic acid, a polymeric sulfonic acid, a sulfated polymer, a polymeric phosphoric acid, and mixtures thereof.

2. The method of claim 1 wherein the composition forms a barrier layer comprising the organic acid on the surface.

3. The method of claim 2 wherein an essentially continuous layer comprising the organic acid is formed on the surface.

4. The method of claim 1 wherein the virus is an acid-labile virus.

5. The method of claim 4 wherein the acid-labile virus comprises a rhinovirus serotype.

6. The method of claim 1 wherein the virus comprises a rotavirus serotype.

7. The method of claim 1 wherein the virus comprises a norovirus.

8. The method of claim 1 wherein the surface is a skin of a mammal.

9. The method of claim 8 wherein the composition lowers a pH of the skin to less than 4 after contact with the skin.

10. The method of claim 1 wherein the surface is an inanimate surface.

11. The method of claim 1 wherein the composition imparts a persistent antiviral activity to the surface.

12. The method of claim 1 wherein the powdered solid substrate is selected from the group consisting of a silica, a clay, a superabsorbent polymer, and mixtures thereof.

13. The method of claim 12 wherein the powdered solid substrate is hydrated.

14. The method of claim 13 wherein the hydrated solid subsrate contains up to about 96%, by weight, water.

15. The method of claim 13 wherein the hydrated solid substrate comprises a hydrophilic silica and water.

16. The method of claim 12 wherein the silica comprises 1,1,1-trimethyl(triethylsilyl)silanamine, trimethyoxy siloxylated silicic acid anhydride, or a mixture thereof.

17. The method of claim 12 wherein the clay is selected from the group consisting of montmorillonite, saponite, nontronite, laponite, beidelite, hectorite, suconite, stevensite, vermiculite, volkonskoite, magadite, medmontite, kenyaite, montmorillonite, sauconite, a kaolin mineral, kaolinite, dickite, nacrite, a serpentine mineral, a mica mineral, illite, a chlorite mineral, sepolite, palygorskite, bauxite, and mixtures thereof.

18. The method of claim 12 wherein the superabsorbent polymer comprises a partially neutralized polyacrylic acid.

19. The method of claim 1 wherein the powdered solid substrate is selected from the group consisting of aluminum silicate, aluminum starch octenylsuccinate, calamine, calcium silicate, cellulose, chalk, corn starch, dextrin, diatomaceous earth, fullers earth, glyceryl starch, kaolin, magnesium aluminum silicate, magnesium carbonate, magnesium hydroxide, magnesium oxide, magnesium silicate, magnesium trisilicate, maltodextrin, microcrystalline cellulose, oat bran, oat flour, oatmeal, potassium aluminum polyacrylate, potato starch, rice starch, silica, talc, wheat starch, and mixtures thereof.

20. The method of claim 1 wherein the powdered solid substrate has an average particle size of about 1 to about 50 nanometers.

21. The method of claim 1 wherein the powdered solid substrate has a particle size distribution of about 0.01 to about 100 nanometers.

22. The method of claim 1 wherein the composition comprises about 0.05% to about 15%, by weight, of the organic acid.

23. The method of claim 1 wherein the polycarboxylic acid comprises an anhydride of a polycarboxylic acid.

24. The method of claim 1 wherein the a polymeric acid has a molecular weight of about 500 to about 10,000,000 g/mol.

25. The method of claim 1 wherein the polymeric acid comprises a homopolymer or a copolymer of acrylic acid.

26. The method of claim 1 wherein the polycarboxylic acid comprises at least two of citric acid, malic acid, and tartaric acid, and the polymeric carboxylic acid comprises a homopolymer or a copolymer of acrylic acid, methacrylic acid, or mixtures thereof.

27. The method of claim 1 wherein the polycarboxylic acid comprises citric acid, malic acid, tartaric acid, and mixtures thereof.

28. The method of claim 9 wherein the skin of the mammal has a skin pH of less than 4 four hours after contact.

29. The method of claim 1 wherein rhinoviruses, picornaviruses, adenoviruses, rotaviruses, influenza viruses, herpes viruses, respiratory syncytial viruses, coronaviruses, entereoviruses, and similar pathogenic viruses are inactivated.

30. The method of claim 1 wherein the composition is applied prior to the surface being exposed to a virus.

31. The method of claim 1 wherein the composition is applied multiple times within a twenty-four hour period.

32. The method of claim 2 wherein a virucidally effective amount of the organic acid remains in the barrier layer on the surface after ten rinsings with water.

33. The method of claim 1 wherein at least 50%, by weight, of the nonvolatile components of the composition are present on the surface after three rinses with water.

34. A method of reducing a virus population on a surface comprising contacting the surface with a solid composition comprising:
   a) a powdered solid substrate; and
   b) a virucidally effective amount of an organic acid comprising (i) two or more polycarboxylic acids selected from the group consisting of malonic acid, succinic acid, glutaric acid, adipic acid, pimelic acid, suberic acid, azelaic acid, sebacic acid, fumaric acid, maleic acid, tartaric acid, malic acid, maleic acid, citric acid, aconitic acid, and mixtures thereof, and (ii) a polymeric acid having a plurality of carboxylic, phosphate, sulfonate, and/or sulfate moieties, wherein the composition, after contact with water, has a pH of about 2 to less than about 5 at 25° C.

35. A method of reducing a virus population on a surface comprising contacting the surface with a solid composition comprising:
   a) a powdered solid substrate; and
   b) a virucidally effective amount of an oranic acid comprising (i) two or more polycarboxylic acids selected from the group consisting of malonic acid, succinic acid, glutaric acid, adipic acid, pimelic acid, suberic acid, azelaic acid. sebacic acid, fumaric acid, maleic acid, tartaric acid, malic acid, maleic acid, citric acid, aconitic acid, and mixtures thereof, and (ii) a polymeric acid having a plurality ofcarboxylic, phosphate, sulfonate, and/or sulfate moieties,
   wherein the composition is free of an anionic, cationic, and ampholytic surfactants.

36. A method of reducings a virus population on a surface comprising contacting thc surface with a solid composition comprising:
   a) a powdered solid substrate; and
   b) a virucidally effective amount of an organic acid comprising (i) two or more polycarboxylic acids selected from the group consisting of malonic acid, succinic acid, glutaric acid, adipic acid, pimelic acid, suberic acid, azelaic acid, sebacic acid, fumaric acid, maleic acid, tartaric acid, malic acid, maleic acid, citric acid, aconitic acid, and mixtures thereof, and (ii) a polymeric acid having a plurality of carboxylic, phosphate, sulfonate, and/or sulfate moieties,
   wherein the composition further comprises an active antimicrobial agent, an alcohol, or a mixture thereof.

37. A method of reducing a virus population on a surface comprising contacting the surface with a solid composition comprising:
   a) a powdered solid substrate; and
   b) a virucidally effective amount of an organic acid comprising (i) two or more polycarboxylic acids selected from the group consisting of malonic acid, succinic acid, glutaric acid, adipic acid, pimelic acid, suberic acid, azelaic acid, sebacic acid, fumaric acid, maleic acid, tartaric acid, malic acid, maleic acid, citric acid, aconitic acid, and mixtures thereof, and (ii) a polymeric acid having a plurality of carboxylic, phosphate, sulfonate, and/or sulfate moieties,
   wherein the contacted surface has a log reduction of at least 3 against a nonenveloped virus at least about four hours after contact.

38. The method of claim 37 wherein the contacted surface has a log reduction of at least 2 against a nonenveloped virus about six hours after contact.

39. A method of reducing a virus population on a surface comprising contacting he surface with a solid composition comprising:
   a) a powdered solid substrate; and
   b) a virucidally effective amount of an organic acid comprising (i) two or more polycarboxylic acids selected from the group consisting of malonic acid, succinic acid, glutaric acid, adipic acid, pimelic acid, suberic acid, azelaic acid, sebacic acid, fumaric acid, maleic acid, tartaric acid, malic acid, maleic acid, citric acid, aconitic acid, and mixtures thereof, and (ii) a polymeric acid having a plurality of carboxylic, phosphate, sulfonate, and/or sulfate moieties,
   wherein the polymeric acid is present in the solid composition in an amount of about 0.1% to about 2%, by weight of the solid composition.

* * * * *